(12) United States Patent
Tjin et al.

(10) Patent No.: US 8,173,973 B2
(45) Date of Patent: May 8, 2012

(54) ELIMINATING FLUORESCENCE BACKGROUND NOISE

(75) Inventors: Swee Chuan Tjin, Singapore (SG); Lian Soon Ng, Singapore (SG); Cheong Boon Soh, Singapore (SG); Rudi Irawan, Singapore (SG); Xiaoqin Fang, Singapore (SG)

(73) Assignee: Nanyang Technological University, Singapore (SG)

( * ) Notice: Subject to any disclaimer, the term of this patent is extended or adjusted under 35 U.S.C. 154(b) by 777 days.

(21) Appl. No.: 12/089,306

(22) PCT Filed: Oct. 6, 2005

(86) PCT No.: PCT/SG2005/000343
§ 371 (c)(1),
(2), (4) Date: Oct. 29, 2008

(87) PCT Pub. No.: WO2007/040459
PCT Pub. Date: Apr. 12, 2007

(65) Prior Publication Data
US 2009/0218515 A1 Sep. 3, 2009

(51) Int. Cl.
*G01J 1/58* (2006.01)

(52) U.S. Cl. .................... 250/459.1; 250/458.1

(58) Field of Classification Search ............ 250/458.1, 250/459.1
See application file for complete search history.

(56) References Cited

U.S. PATENT DOCUMENTS

| 5,270,548 A | 12/1993 | Steinkamp |
| 5,340,715 A * | 8/1994 | Slovacek et al. ............ 435/6 |
| 2002/0092973 A1 * | 7/2002 | Nagle et al. ............ 250/216 |

FOREIGN PATENT DOCUMENTS

WO    WO 01/09605 A1    2/2001

OTHER PUBLICATIONS

Booth et al., "Low-cost frequency domain fluorescence lifetime confocal microscopy", *J Microsc.* (2004) 214(1):36-42.
International Preliminary Report on Patentability dated Apr. 8, 2008 in PCT/SG2005/000343, filed Oct. 6, 2005.

* cited by examiner

*Primary Examiner* — Mark R Gaworecki
(74) *Attorney, Agent, or Firm* — Knobbe Martens Olson & Bear LLP

(57) ABSTRACT

A method for measuring a fluorescent sample on a substrate. The method includes exciting the fluorescent sample with an exciting light source for the generation of a sample fluorescent optical signal and a substrate fluorescent optical signal substantially eliminated. The microfluidic substrate fluorescent optical signal is leaving the sample fluorescent optical signal. The sample fluorescence optical signal can then be processed.

34 Claims, 18 Drawing Sheets

ELIMINATING FLUORESCENCE BACKGROUND NOISE

FIELD OF THE INVENTION

The invention relates to a method and apparatus for measuring a fluorescent sample on a substrate and preferably, though not exclusively, relates to a method and apparatus for measuring a fluorescent sample within a microfluidic channel of a microfluidic substrate.

DEFINITIONS

Throughout this specification a reference to a fluorescent sample is to be taken as including a naturally fluorescent sample as well as a fluorescently labeled sample.

Throughout this specification a reference to a substrate is to be taken as a reference to a product, or component of a product, that is able to absorb an exciting radiation at a wavelength, and remit the radiation at a higher wavelength.

BACKGROUND OF THE INVENTION

For many years, medical diagnostic tools have used classical biochemical techniques that involve bulky and expensive equipment such as spectrophotometry, gas chromatography (GC), mass spectrometry (MS), high-performance liquid chromatography (HPLC), paper and thin-layer chromatography (PC and TLC), and electrophoretic techniques coupled with fluorescence detection techniques. These standard analytical tools work effectively and efficiently. However, the tools are expensive, and they require costly consumables, sample throughput, and experienced and skilled operators. All these hinder rapid, inexpensive, and in-situ diagnosis of health-care requirements. Furthermore, such methods often require tedious and laborious processes. For these reasons, these tools are mostly used as confirmatory tools for the presumptive positive samples that are initially screened by some types of assay techniques.

Currently, the problems with quantitative immunoassay techniques are not significantly different from the classical biochemical techniques mentioned earlier. The performance of quantitative immunoassays is today largely restricted to centralized laboratories because of the need for long assay times, and relatively complex, bulky and expensive equipment, as well as highly trained operators. Most immunoassays remain within the walls of large centralized laboratories, far from the patients whose samples are collected and measured. If a wider range of the immunoassays are able to be run in a simpler way, less expensively and at the point of care or in the home health care environment, the health of many patients may be improved. To achieve this objective, a simple, compact, smart, robust, and inexpensive device providing high quality results is required.

Optical biosensors have some advantages, such as sensitivity, simplicity and immunity to electromagnetic wave interferences. Due to these advantages, optical biosensors are one type of biosensor exploited for immunoassay applications. There are many types of optical techniques which are commonly used for biosensing applications. Fluorescence-based sensors are highly developed due to their high sensitivity, versatility, accuracy and fairly good selectivity. A fluorescence method is also very suitable for miniaturization. The current technology to measure/detect fluorescent samples on a substrate such as, for example, inside a microfluidic channel, is performed by focusing the excitation light source onto the sample inside the microchannel and collecting the fluorescence emission of the sample using a set of complex lenses, mirrors, and optical filters. As a result, the fluorescence signal of microfluidic substrates may enter the detection system giving rise to a strong but unwanted fluorescence noise. The fluorescence from the sample of interest is usually very weak due to the low sample concentration. As a consequence, fluorescence noise due to the fluorescence of substrate may suppress the desired fluorescence signal from the sample of interest.

Currently, there are two approaches commonly used to avoid the noise due to the fluorescence of the substrate. The first approach is to incorporate a confocal fluorescence microscope to block the signals not from the thin layer within which the sample resides. This technique requires bulky, expensive and complicated optics. In the second approach, materials are selected with the substrate material having no, or a low, fluorescence property. Optical grade glass and silica are commonly used, since these materials do not fluoresce when they are excited by light within the visible wavelength range. However, these materials are relatively expensive and fabrication of microfluidic channels using these materials requires time-consuming photomask generation, photolithography and etching processes. As a consequence, a microfluidic chip made from optical grade glass or silica is relatively expensive.

Possible inexpensive materials suitable as substrate materials are polymer-based materials, such as polymethyl-methacrylate (PMMA), polycarbonate and Mylar. In addition, microfluidic channels using polymeric materials are easily fabricated by molding, embossing, casting or ablation processes. Complex models of microchannels in polymer sheets can be fabricated in less than an hour using a direct-write laser system. However, these materials exhibit relatively high fluorescence signals which in turn hinder their use for low fluorescence intensity detection. The intensity of the fluorescence background signal from the polymeric materials may be two orders of magnitude higher than the fluorescence signal of a sample within the microfluidic channel. Hence, there is a need to address the auto-fluorescence background noise of polymeric materials used in a polymeric microfluidic chip.

SUMMARY OF THE INVENTION

In accordance with a first preferred aspect there is provided a method for measuring a fluorescent sample on a substrate. The method comprises exciting the fluorescent sample with an exciting light source for the generation of a sample fluorescent optical signal and a substrate fluorescent optical signal. The substrate fluorescent optical signal is substantially eliminated leaving the sample fluorescent optical signal. The sample fluorescence optical signal is then processed. The substrate may be a microfluidic channel of a microfluidic substrate.

The substantially eliminating the substrate fluorescence signal may be by:
 (a) modulating the frequency of a light source to excite the fluorophore of the sample according to a predetermined modulation frequency such that the phase difference between the sample fluorescence optical signal and the substrate fluorescence optical signal is substantially 90°;
 (b) generating a sine wave signal based on a unity-gain sine wave signal corresponding to the predetermined modulation frequency delayed by the phase of the sample fluorescence optical signal;
 (c) mixing the two sine wave signals with an acquired signal corresponding to the fluorescence emission of the sample and the substrate, into at least one mixed signal; and (d) filtering the at least one mixed signal to obtain a DC component of the fluorescence signal of the sample;
(e) wherein the fluorescence emission of the substrate is filtered and the DC component is proportional to the concentration of the fluorescence signal of the sample.

Alternatively, the substantially eliminating the substrate fluorescence signal may be by:
(a) modulating the frequency of a light source to excite the fluorophore of the sample according to a predetermined modulation frequency;
(b) generating a unity-gain square wave of the same frequency as a sample fluorescence optical signal; the unity-gain square wave serving as a switching signal for mixing;
(c) mixing the unity-gain square wave with an acquired signal corresponding to the fluorescence emissions of the sample and the substrate, into at least one mixed signal;
(d) using the switching signal to modulate the sample fluorescence optical signal and the substrate fluorescence optical signal to create a phase difference between them;
(e) filtering the at least one mixed signal to obtain a DC component of the fluorescence signal of the sample;
(f) wherein the fluorescence emission of the substrate is filtered and the DC component is proportional to the concentration of the fluorescence signal of the sample.

Further alternatively, the substantially eliminating the substrate fluorescence signal may be by:
(a) modulating the frequency of a light source before introduction of the sample onto the substrate so as to generate a substrate fluorescence optical signal;
(b) using the substrate fluorescence optical signal to generate a generated signal which is in phase with the substrate fluorescence optical signal;
(c) introducing the sample onto the substrate and modulating the frequency of the light source to excite the fluorophore of the sample according to a predetermined modulation frequency such that a phase difference exists between the sample fluorescence optical signal and the substrate fluorescence optical signal;
(d) generating a sine wave based on a unity-gain sine wave signal corresponding to the predetermined modulation frequency but with a phase difference of 90 degrees with respect to the phase of the generated signal;
(e) mixing the sine wave signal with an acquired signal corresponding to the fluorescence emission of the sample and the substrate, into at least one mixed signal; and
(f) filtering the at least one mixed signal to obtain a DC component of the fluorescence signal of the sample;
(g) wherein the fluorescence emission of the substrate is filtered and the DC component is proportional to the concentration of the fluorescence signal of the sample.

According to a second preferred aspect there is provided a method for measuring a fluorescent sample on a substrate, the method comprising:
(a) modulating the frequency of a light source to excite the fluorophore of the sample according to a predetermined modulation frequency such that the phase difference between the sample fluorescence optical signal and the substrate fluorescence optical signal is substantially 90 degrees;
(b) generating a sine wave based on a unity-gain sine wave signal corresponding to the predetermined modulation frequency delayed by the phase of the substrate fluorescence optical signal;
(c) mixing the sine wave signal with an acquired signal corresponding to the fluorescence emission of the sample and the substrate, into at least one mixed signal; and
(d) filtering the at least one mixed signal to obtain a DC component of the fluorescence signal of the sample;
(e) wherein the fluorescence emission of the substrate is filtered and the DC component is proportional to the concentration of the fluorescence signal of the sample.

According to a third preferred aspect there is provided a method for measuring a fluorescent sample on a substrate, the method comprising:
(a) modulating the frequency of a light source to excite the fluorophore of the sample according to a predetermined modulation frequency;
(b) generating a unity-gain square wave of the same frequency as a sample fluorescence optical signal; the unity-gain square wave serving as a switching signal for mixing;
(c) mixing the unity-gain square wave with an acquired signal corresponding to the fluorescence emissions of the sample and the substrate, into at least one mixed signal;
(d) using the switching signal to modulate the sample fluorescence optical signal and the microfluidic substrate fluorescence optical signal to create a phase difference between them;
(e) filtering the at least one mixed signal to obtain a DC component of the fluorescence signal of the sample;
(f) wherein the fluorescence emission of the substrate is filtered and the DC component is proportional to the concentration of the fluorescence signal of the sample.

According to a fourth preferred aspect there is provided a method for measuring a fluorescent sample on a substrate, the method comprising:
(a) modulating the frequency of a light source before introduction of the sample onto the substrate so as to generate a substrate fluorescence optical signal;
(b) using the substrate fluorescence optical signal to generate a generated signal which is in phase with the substrate fluorescence optical signal;
(c) introducing the sample onto the substrate and modulating the frequency of the light source to excite the fluorophore of the sample according to a predetermined modulation frequency such that there is a phase difference between the sample fluorescence optical signal and the substrate fluorescence optical signal;
(d) generating a sine wave based on a unity-gain sine wave signal corresponding to the predetermined modulation frequency and with a phase difference of 90 degrees with respect to the phase of the generated signal;
(e) mixing the sine wave signal with an acquired signal corresponding to the fluorescence emission of the sample and the substrate, into at least one mixed signal; and
(f) filtering the at least one mixed signal to obtain a DC component of the fluorescence signal of the sample;
(g) wherein the fluorescence emission of the substrate is filtered and the DC component is proportional to the concentration of the fluorescence signal of the sample.

The filter may be low-pass filter; and the acquired signal may be acquired by an optical receiver. The unity-gain sine wave signal may be generated by a phase-locked loop ("PLL") circuit. A quadrature phase shifter may generate the two sine wave signals, which may be 90° out of phase with each other. The unity-gain square wave signal may be in phase with the fluorescence signal of the sample.

The fluorophore may be a label, and the label may be fluorescein. The light source may be a 470 nm blue LED with 3460 mcd in intensity.

The PLL circuit may comprise a phase detector to generate an average DC voltage proportional to the phase difference, a low-pass filter (LPF1) to suppress high frequency components generated by the phase detector, and a voltage-controlled oscillator (VCO) to control the VCO frequency to oscillate at a frequency identical to the input frequency with a finite phase difference.

The substrate may be a microfluidic substrate having at least one microfluidic channel. The microfluidic substrate may be made of a polycarbonate material.

The optical receiver may be any one from the group consisting of: photodiode, avalanche photodiode, photomultiplier tube and CCD detector. An optical filter may filter off signals with a wavelength outside the range of interest.

According to a fifth aspect there is provided an apparatus for measuring a fluorescent sample on a substrate, the method comprising:
- (a) a light source for exciting the fluorescent sample for the generation of a sample fluorescent optical signal and a substrate fluorescent optical signal;
- (b) a filtering circuit for substantially eliminating the substrate fluorescent optical signal and leaving the sample fluorescent optical signal; and
- (c) processing apparatus for processing the sample fluorescence optical signal.

The filtering circuit may be an electrical filtering circuit and may comprise:
- (a) a modulator for modulating the frequency of the light source to excite the fluorophore of the sample according to a predetermined modulation frequency such that the phase difference between the sample fluorescence optical signal and the substrate fluorescence optical signal is substantially 90°;
- (b) a signal generator for generating a sine wave signal based on a unity-gain sine wave signal corresponding to the predetermined modulation frequency delayed by the phase of the substrate fluorescence optical signal;
- (c) a mixer for mixing the sine wave signal with an acquired signal corresponding to the fluorescence emission of the sample and the substrate, into at least one mixed signal; and
- (d) a filter for filtering the at least one mixed signal to obtain a DC component of the fluorescence signal of the sample;

Alternatively, the electrical filtering circuit may comprise:
- (a) a modulator for modulating the frequency of the light source to excite the fluorophore of the sample according to a predetermined modulation frequency;
- (b) a signal generator for generating a unity-gain square wave of the same frequency as a sample fluorescence optical signal; the unity-gain square wave serving as a switching signal for mixing;
- (c) a mixer for mixing the unity-gain square wave with an acquired signal corresponding to the fluorescence emissions of the sample and the substrate, into at least one mixed signal; and for using the switching signal to modulate the sample fluorescence optical signal and the substrate fluorescence optical signal to create a phase difference between them;
- (d) a filter for filtering the at least one mixed signal to obtain a DC component of the fluorescence signal of the sample.

Further alternatively, the electrical filtering circuit may comprise:
- (a) a modulator for modulating the frequency of a light source before introduction of the sample onto the substrate so as to generate a substrate fluorescence signal;
- (b) a calibrator for using the substrate fluorescence signal to generate a generated signal which is in phase with the substrate fluorescence signal;
- (c) the modulator also being for modulating the frequency of a light source to excite the fluorophore of the sample, after introduction of the sample onto the substrate, according to a predetermined modulation frequency such that there exist a phase difference between the sample fluorescence optical signal and the substrate fluorescence optical signal;
- (d) a signal generator for generating a sine wave signal based on a unity-gain sine wave signal corresponding to the predetermined modulation frequency and with a phase difference of 90 degrees with respect to the phase of the generated signal;
- (e) a mixer for mixing the sine wave signal with an acquired signal corresponding to the fluorescence emission of the sample and the substrate, into at least one mixed signal; and
- (f) a filter for filtering the at least one mixed signal to obtain a DC component of the fluorescence signal of the sample.

According to a sixth preferred aspect there is provided an apparatus for measuring a fluorescent sample on a substrate, the apparatus comprising:
- (a) a modulator for modulating the frequency of the light source to excite the fluorophore of the sample according to a predetermined modulation frequency such that the phase difference between the sample fluorescence optical signal and the substrate fluorescence optical signal is substantially 90 degrees;
- (b) a signal generator for generating a sine wave signal based on a unity-gain sine wave signal corresponding to the predetermined modulation frequency delayed by the phase of the substrate fluorescence optical signal;
- (c) a mixer for mixing the sine wave signal with an acquired signal corresponding to the fluorescence emission of the sample and the substrate, into at least one mixed signal; and
- (d) a filter for filtering the at least one mixed signal to obtain a DC component of the fluorescence signal of the sample.

According to a seventh aspect there is provided an apparatus for measuring a fluorescent sample on a substrate, the apparatus comprising:
- (a) a modulator for modulating the frequency of the light source to excite the fluorophore label of the sample according to a predetermined modulation frequency;
- (b) a signal generator for generating a unity-gain square wave of the same frequency as a sample fluorescence optical signal; the unity-gain square wave serving as a switching signal for mixing;
- (c) a mixer for mixing the unity-gain square wave with an acquired signal corresponding to the fluorescence emissions of the sample and the substrate, into at least one mixed signal; and for using the switching signal to modulate the sample fluorescence optical signal and the microfluidic substrate fluorescence optical signal to create a phase difference between them; and
- (e) a filter for filtering the at least one mixed signal to obtain a DC component of the fluorescence signal of the sample.

According to an eighth preferred aspect there is provide an apparatus for measuring a fluorescent sample on a substrate, the apparatus comprising:

(a) a modulator for modulating the frequency of a light source before introduction of the sample onto the substrate so as to generate a substrate fluorescence optical signal;

(b) a calibrator for using the substrate fluorescence optical signal to generate a generated signal which is in phase with the substrate fluorescence optical signal;

(c) the modulator also being a modulating the frequency of the light source to excite the fluorophore of the sample, after introduction of the sample onto the substrate, according to a predetermined modulation frequency such that there exist a phase difference between the sample fluorescence optical signal and the substrate fluorescence optical signal (d) a signal generator for generating a sine wave signal based on a unity-gain sine wave signal corresponding to the predetermined modulation frequency and with a phase difference of 90 degrees with respect to the phase of the generated signal;

(e) a mixer for mixing the sine wave signal with an acquired signal corresponding to the fluorescence emission of the sample and the substrate, into at least one mixed signal; and (f) a filter for filtering the at least one mixed signal to obtain a DC component of the fluorescence signal of the sample.

The present invention provides a method to eliminate the noise from the fluorescence of the substrate (background noise) by filtering of the fluorescence signals. The method may use combination of one or more of: a phase-locked loop, quadrature demodulator and annihilator circuits. Preferably, the method is able to completely eliminate the fluorescence noise from substrate materials so that very weak fluorescence signal arising from the low concentration sample of interest is detectable.

Advantageously, the present invention is able to discriminate a very weak fluorescence signal of sample of interest from a large unwanted fluorescence signal caused by the fluorescence background of the microfluidic substrate. Hence, the present invention may enable detection of very low concentrations of a sample of interest on a substrate made of materials with high fluorescence properties, such as polymeric sheet materials.

BRIEF DESCRIPTION OF THE DRAWINGS

In order that the present invention may be fully understood and readily put into practical effect, there shall now be described by way of non-limitative example only preferred embodiments of the present invention, the description being with reference to the accompanying illustrative drawings.

In the drawings.

DETAILED DESCRIPTION OF THE PREFERRED EMBODIMENTS

Due to the difference in fluorescent emission lifetime of the fluorescein and the substrate, a phase difference in two output signals can be created.

When a fluorescent sample is excited by modulated light source of appropriate wavelength, the sample will fluoresce with the same frequency but will be phase shifted with respect to the exciting source by an amount proportional to the fluorescence lifetime of the sample. The fluorescent intensity of the sample, in this case, can be simply extracted by optical filtering of the wavelength of the exciting light source. However, if there are two fluorescent samples with similar fluorescence wavelengths but with slightly different lifetimes, optical filtering will only remove the signal from the excitation light source but will not be able to separate the information encoded in the two fluorescence samples. Due to the difference in their fluorescence lifetimes, the fluorescence signal from the two samples will be phase shifted by different amounts. The method proposed here aims to substantially eliminate the fluorescence signal from one of the samples, which we refer to as the background or substrate signal, so as to enhance the signal from the sample of interest.

Figure 1:
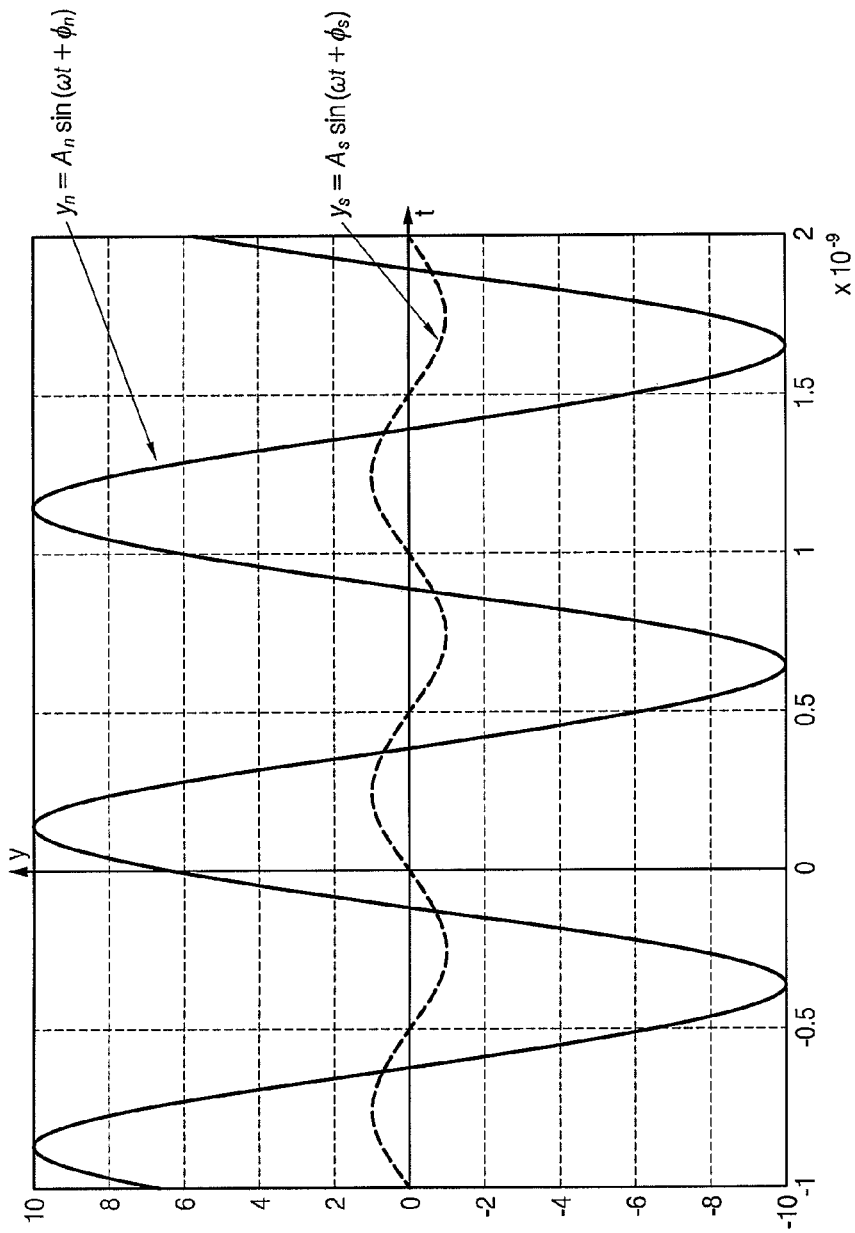
FIG. 1 is an illustration of a weak fluorescence desired signal and higher intensity of an unwanted auto-fluorescence signal from a microfluidic substrate.

Referring to FIG. 1, when the excitation light is modulated to a frequency $f_{mod}$, is incident on the surface of the fluorescent sample inside the microfluidic channel made of a polymer, two sets of signals are produced, assuming that the excitation signal has already been filtered off. They are: (1) the fluorescence signal emitted by the sample of interest; and (2) the fluorescence background noise emitted by the substrate. These two sets of signals have the same modulating frequency as the incident light source, but, in general, are at a different phase and amplitude with respect to the incident oscillating light source due to the difference in their fluorescence lifetime. As the sample of interest within a microfluidic channel may be very low in concentration, it will form the weaker of the two signals. This weak signal is denoted as $y_s(t)=A_s \sin(\omega t+\phi_s)$ where $\omega=2\pi f_{mod}$. The stronger signal is the unwanted signal, as it represents the fluorescence background noise from the substrate. This is denoted as $y_n(t)=A_n \sin(\omega t+\phi_n)$. Generally, the fluorescence signals from the sample of interest and the substrate have different fluorescence lifetimes. Thus there is a phase difference between $y_s(t)$ and $y_n(t)$. The phase difference of the two signals with respect to the incident signal is denoted as $\phi_s$ and $\phi_n$ respectively. To detect the weaker fluorescence desired signal $y_s(t)$, a phase-locked loop and quadrature demodulator method for eliminating the stronger unwanted auto-fluorescence noise signal $y_n(t)$ is used. This method is able to eliminate the auto-fluorescence background noise, so that the very weak fluorescence signal generated by the sample of interest is detectable and measurable.

Eight embodiments of implementing the method may be used. The first embodiment uses a combination of phase-locked loop and quadrature demodulation techniques. This embodiment is suitable if the phase difference between the desired signal and the unwanted signal is close to 90°. The second embodiment uses a phase-locked loop technique only, which is more general, and used to minimize the background noise for signals with phase difference that is not close to 90°. The third embodiment uses a combination of phase-locked loop and quadrature annihilator techniques. This embodiment is suitable provided there is a phase difference between the desired signal and the unwanted signal. The fourth uses quadrature demodulator and phase locked loop systems, and the fifth uses only the quadrature demodulator. The sixth uses a quadrature annihilator and a phase-locked loop; whereas the seventh and eighth both use a quadrature annihilator.

I. First Embodiment

Using Quadrature Demodulator and Phase-locked Loop

Figure 2:
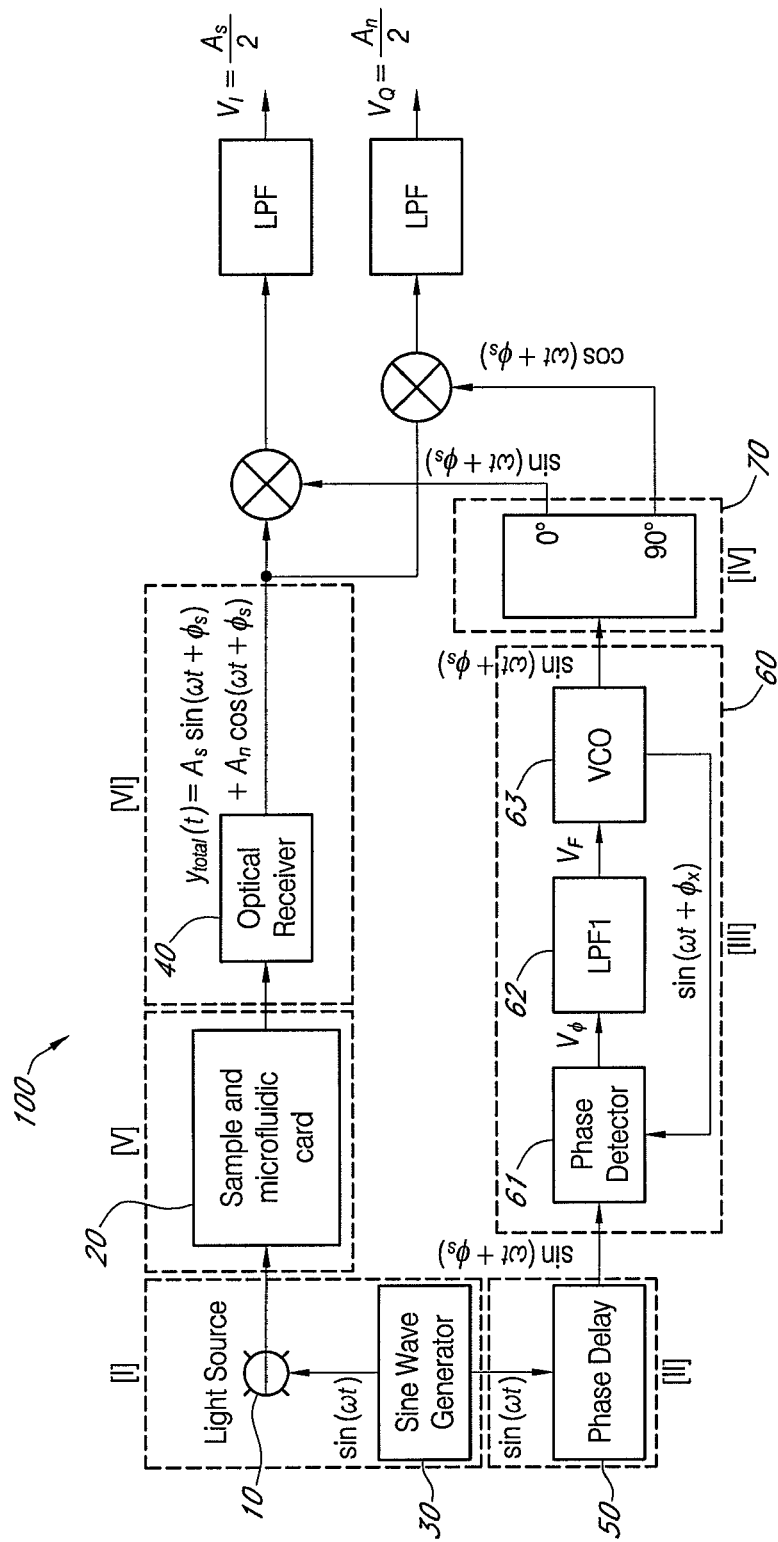
FIG. 2 is a layout of a first embodiment for fluorescence noise elimination.

Referring to FIG. 2, the system 100 comprises six main blocks: the tunable modulated light source system [I], the phase delay generator [II], the phase-locked loop circuitry [III], the quadrature phase shifter [IV], the sample 20 (sample and microfluidic card) [V], and the optical receiver [VI].

1.1 Light-Source [1]

Different light sources may be used as the excitation light source 10. Examples are lasers of appropriate wavelength including laser diodes, LEDs or a broadband light source. The wavelength of the light source 10 must be able to excite the fluorophore of the sample. For an example, if the fluorophore is fluorescein label, a light source 10 with a wavelength between 450 nm and 500 nm is required. Ideally, the wavelength of the light source 10 should only have a single wavelength, for example, light emitted by a laser or laser diode. However, a laser source is usually relatively bulky and expensive. In addition, lasers and laser diodes are only available at certain wavelengths. These may not be suitable for certain types of fluorophores and chromophores. If the light source 10 is an LED that covers the excitation wavelength region and also the fluorescence wavelength region, a suitable low-pass optical filter or band-pass optical filter is installed between the LED and the microfluidic card. The light beam, particularly from an LED, diverges, so that a focusing lens system is required to focus the light into the sample 20 inside the microfluidic channel.

The intensity of fluorescence emissions from the sample and the substrate is proportional to the intensity of excitation light source 10. However, if the intensity of light source 10 is too high, it may cause quick photodestruction or photobleaching of the fluorophore. Experiments have shown that a 470 nm blue LED with 3460 mcd in intensity is sufficient to excite fluorescein.

For the purpose of the noise elimination method proposed in this first embodiment, the light source 10 must be modulated at a frequency such that the phase difference between the fluorescence desired signal and unwanted signal is 90°. The modulation frequency to achieve this condition depends on the difference between the fluorescence lifetime of fluorophore of the sample and substrate. The modulation frequency is calculated using equation (1) as follows:

$$f_{mod} = \frac{1}{4(\Delta t)} \quad (1)$$

where $\Delta t$ is fluorescence lifetime difference between the labeled sample and the substrate.

As an example, if $\Delta t = 1$ ns, the $f_{mod} = 250$ MHz. From tests, in general, an LED can only be modulated up to 50 MHz. Therefore, if a high frequency modulation is required, a laser source or laser diode may have to be used.

1.2 Phase Delay Generator

The phase delay generator 50 is used to shift the phase of the sine wave signal generated by the sine wave generator 30. The sine wave signal is used to modulate the light source 10. The phase delay may be manually tuned. In this embodiment, the phase delay is carefully tuned to $\phi_s$, where $\phi_s$ is the phase of the desired fluorescence signal, so that the output of phase delay generator 50 is $\sin(\omega t + \phi_s)$. This output of the phase delay generator 50 is input into the phase-locked loop circuitry to ensure the phase is locked.

1.3 Phase-Locked Loop ("PLL") System

A simple PLL system 60 comprises a phase detector 61, low-pass filter (LPF1) 62 and voltage-controlled oscillator ("VCO") 63. The modulating signal, $\sin(\omega t)$, generated by the sine wave generator 30 is firstly delayed, either manually or automatically, by a certain phase $\phi_s$. If the locked condition is achieved, the frequency and the phase of the PLL system output are similar to the frequency and the phase of the desired signal. The phase detector 61 serves as an "error amplifier" in the feedback loop, which minimizes the phase difference, $\Delta\phi = \phi_s - \phi_o \approx 0$, between the delayed modulating signal and the output signal of the VCO 63. The loop is considered locked if $\Delta\phi \approx 0$ is invariant with time, and the input and output frequencies are equal.

Under the phase-locked condition, all the signals in the loop reach a steady state. The phase detector 61 generates an average DC voltage that is proportional to $\Delta\phi$. Referring to FIG. 2, the LPF1 62 suppresses the high-frequency components generated by the phase detector 61 since the phase detector 61 is a multiplier which usually produces harmonics. The DC value of the DC voltage is input to the VCO 63 to control the VCO frequency. The VCO frequency oscillates at a frequency identical to the input frequency with a finite phase difference, $\Delta\phi = \phi_s - \phi_o$. This signal is required to produce the necessary error voltage that will shift the VCO frequency, while maintaining the loop in locked condition. With sufficiently high loop gain of the PLL 60, the phase error is minimized.

The output signal of the VCO 63 may be a unity-gain sine wave signal, $\sin(\omega t + \phi_s)$, which has the same frequency and phase as the signal to be detected, $y_s(t)$.

1.4 Quadrature Phase Shifter

If the modulation frequency for the light source 10 is carefully tuned, the unwanted noise signal $y_n$ is 90° out of phase to the desired signal $y_s$. Hence, the output of the optical receiver 40 becomes:

$$y(t)_{total} = y_s + y_n \quad (2)$$
$$= A_s \sin(\omega t + \phi_s) + A_n \cos(\omega t + \phi_s)$$

The output of the PLL 60, sin $(\omega t+\phi_s)$, is then input to the quadrature phase shifter 70, to generate two sine wave signals which are 90° out of phase with each other, that is, $i(t)=\sin(\omega t+\phi_s)$ and $q(t)=\cos(\omega t+\phi_s)$. These two signals are input into a respective mixer and both are mixed with the signal generated by the optical receiver 40 $y(t)_{total}$. The output from the mixers comprises DC components and AC components. To obtain the DC components only, the AC components of the mixer output must be filtered off. After filtering by two low-pass filters, two respective DC signals, the desired DC signal $$V_i = \frac{A_s}{2}$$

and unwanted DC signal due to the fluorescence of the substrate $$V_q = \frac{A_n}{2},$$

are generated. The mathematical basis for this technique is described later.

These results show the generation of a pure DC component of the desired/signal $$V_i = \frac{A_s}{2}$$

is generated. It also demonstrates that this method is able to filter off the noise to generate only DC components of the desired signal. The DC components of the desired signal are proportional to the peak intensity of the modulated fluorescence desired signal. This technique simplifies the signal measurement and data processing. A volt-meter is able to measure the output of the fluorescence detection system 100. Hence, the value of the DC level of $V_i$ indicates the concentration of the sample.

1.5 Sample and Microfluidic Card

Microfluidic channels are constructed in a microfluidic card. Microfluidic channels based on polycarbonate materials, such as PMMA and Mylar, are relatively cheap and easily fabricated. Thus, polycarbonate materials are an important commercial material for microfluidic applications. Microfluidic cards are often considered a consumable item. However, the fluorescence background of polycarbonate materials is considerably high, particularly compared to the fluorescence intensity of the sample of interest immobilized inside a microfluidic channel.

Figure 3:
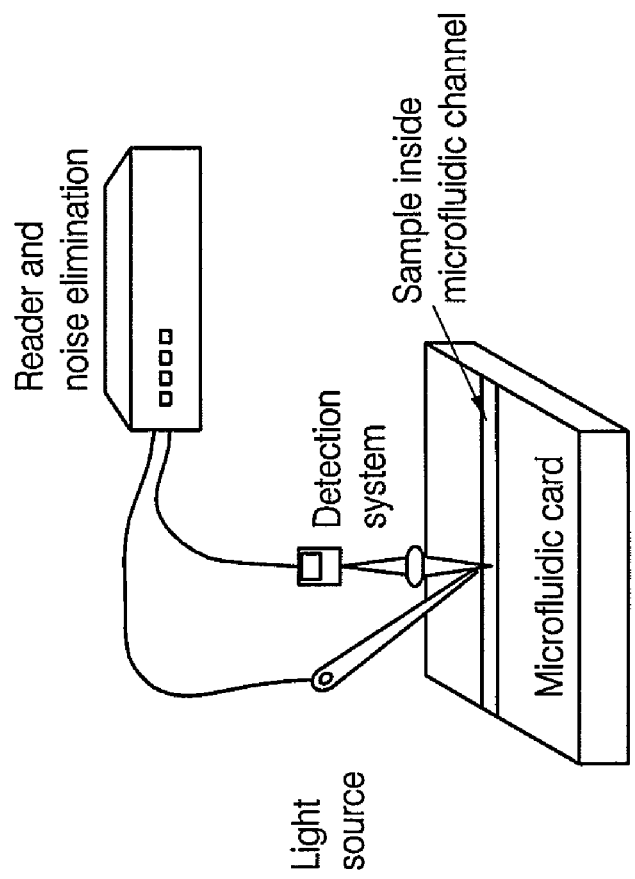
FIG. 3 is a schematic diagram of geometrical configuration of light source, microfluidic card, detector, and noise elimination unit.

Referring to FIG. 3, a compact and simple fluorescence detection system 100, detects fluorescence emission of sample of interest, and also other light emissions generated at the illuminated spot, such as fluorescence from microfluidic substrate 20. Therefore, a noise elimination system is crucial in providing a compact, simple, and sensitive microfluidic immunoassay fluorescence detection system 100.

1.6 Optical Receiver

The working region of the optical receiver 40 must cover the fluorescence wavelength of the sample of interest. For example, if the fluorophore used is fluorescein having a fluorescence wavelength range between 500 nm and 600 nm, the optical receiver 40 must be sensitive to this wavelength range. An optical filter, either a long-pass filter or a band-pass filter, may need to be installed before the optical receiver 40, to filter off signals with a wavelength outside the range of interest. As the light source 10 in this embodiment is modulated at a certain modulation frequency, the optical receiver 40 must also be able to respond to the modulated signals at that frequency. There are many types of optical receivers 40 suitable for this embodiment such as photodiodes, avalanche photodiodes, and photomultiplier tubes. A photomultiplier tube is a very sensitive light detector, but the size is relatively bulky, and requires high biasing voltage (1000V). A photodiode is cheap, compact, and simple, but its sensitivity is not as good as a photomultiplier tube and may not be suitable for very weak fluorescence signals. An avalanche photodiode may be used as they are relatively inexpensive, compact, and have good sensitivity. For a multichannel detection system, an array of CCD detectors may be used.

1.7 Step by Step Analysis

The frequency of the light source modulation is carefully tuned so that the phase difference between desired signal $y_s$ and unwanted signal $y_n$ is 90°. That is, they are 90° out of phase.

$$\phi_n = \phi_s + 90°$$

After the optical receiver 40, the signal generated by the sample and microfluidic system 100 is:

$$y_{total} = y_s + y_n \quad (3)$$
$$= A_s \sin(\omega t + \phi_s) + A_n \cos(\omega t + \phi_s)$$

Referring to FIG. 2, this signal can be split into two equal portions which are 90° out of phase with each other, and mixed with the outputs of a quadrature phase shifter 70.

$$i(t) = \sin(\omega t + \phi_s) \quad (4)$$

and $$q(t) = \cos(\omega t + \phi_s) \quad (5)$$

Mixing of (3) and (4) results in:

$$x_i(t) = y_{total}(t) \cdot i(t) \quad (6)$$
$$= [A_s \sin(\omega t + \phi_s) + A_n \cos(\omega t + \phi_s)] \cdot \sin(\omega t + \phi_s)$$
$$= A_s \sin(\omega t + \phi_s)^2 + A_n \cos(\omega t + \phi_s) \sin(\omega t + \phi_s)$$
$$= \frac{A_s}{2} - \frac{A_s}{2} \cos(2\omega t + 2\phi_s) + \frac{A_n}{2} \sin(2\omega t + 2\phi_s)$$

Mixing of (3) and (5) results in:

$$x_q(t) = y_{total}(t) \cdot q(t) \quad (7)$$
$$= [A_s \sin(\omega t + \phi_s) + A_n \cos(\omega t + \phi_s)] \cdot \cos(\omega t + \phi_s)$$
$$= A_s \sin(\omega t + \phi_s)\cos(\omega t + \phi_s) + A_n \cos(\omega t + \phi_s)^2$$
$$= \frac{A_s}{2} \sin(2\omega t + 2\phi_s) + \frac{A_n}{2} + \frac{A_n}{2} \cos(2\omega t + 2\phi_s)$$

There are DC components and AC components in (6) and (7). The AC components are filtered off using low pass filters 80, leaving only respective DC components, that is:

$$V_i = \frac{A_s}{2} \quad (8)$$

and $$V_q = \frac{A_n}{2} \quad (9)$$

Recall from FIG. 2, $$V_i = \frac{A_s}{2}$$

is the desired component, and $$V_q = \frac{A_n}{2}$$

is the unwanted signal. Equation (8) shows that this technique is able to help eliminate the noise due to auto-fluorescence of the substrate. Equation (8) also shows that $$V_i = \frac{A_s}{2}$$

depends only on amplitudes $A_s$ which is proportional to the concentration of the labeled sample, so that the magnitude of DC level of $V_i$ is proportional to the concentration of the sample.

Therefore, after the elimination of the noise due to the auto fluorescence of the substrate, the fluorescence signal of the labeled sample remains and can be subsequently processed to provide the necessary or desired output.

II. Second Embodiment

Using Only Phase-Locked Loop

If the fluorescence lifetime of a sample of interest is almost similar to the fluorescence lifetime of the substrate, a high frequency system, including a light source 10 and detector, is required in order to apply the technique proposed in the first embodiment. The availability of high frequency optical sources and detectors remains problematic due to limitations of the existing technologies. Where a high frequency system in order of GHz is not viable due to technical or cost constraints, the technique proposed in the first embodiment described above can be modified.

Figure 4:
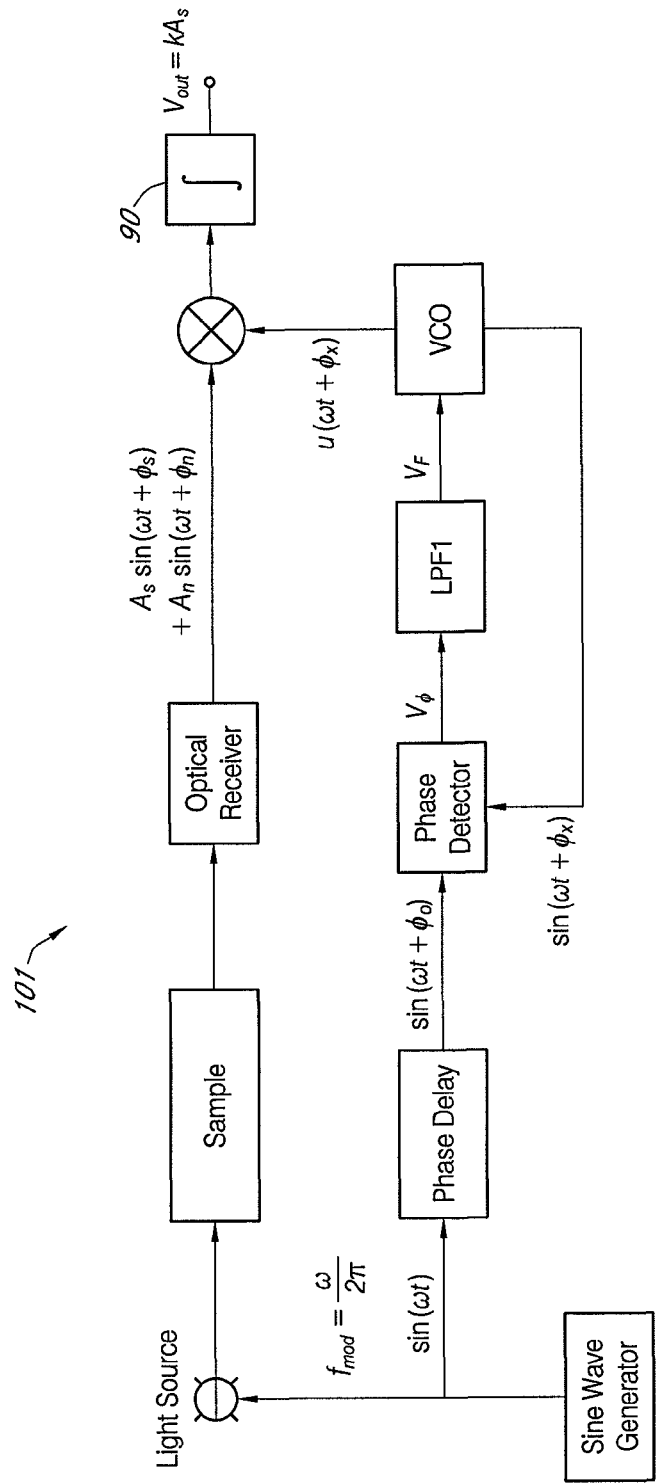
FIG. 4 is a layout of a second embodiment for fluorescence background elimination.

Referring to FIG. 4, a second embodiment is provided which does not require the use of a quadrature phase shifter 70.

Figure 5:
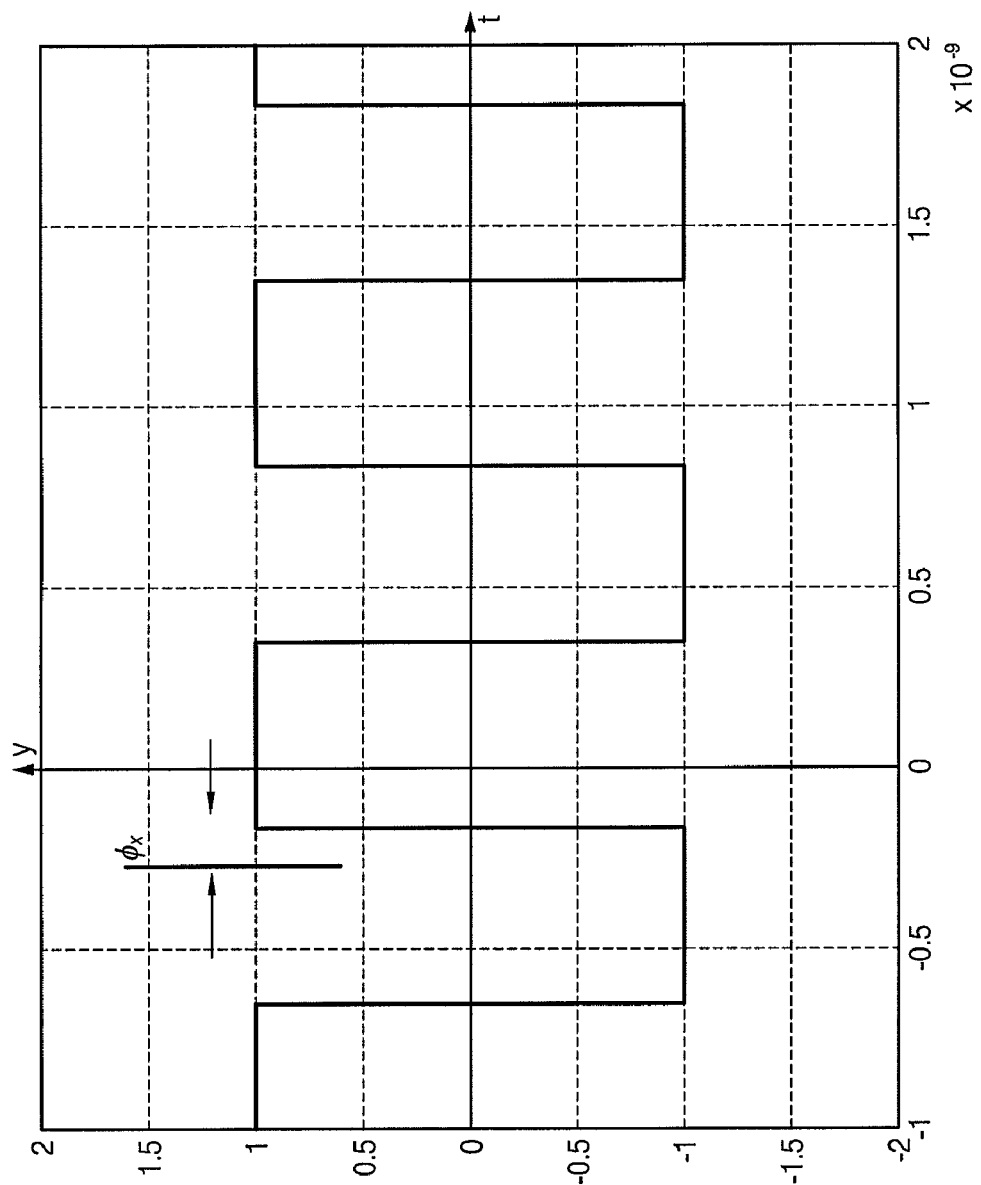
FIG. 5 is an illustration of unity-gain square waves generated by the phase-locked loop (PLL) of FIG. 4.

Referring to FIG. 4, the system 101 uses a PLL 60 similar to the PLL 60 in FIG. 2. However, the output signal of the VCO 63 in this embodiment is a unity-gain square wave, $u(\omega t + \phi_x)$. Referring to FIG. 5, the unity-gain square wave also has the same frequency as the signal to be detected, $y_s(t)$. This square wave serves as the switching signal for the mixer. The fractional phase of $u(t)$ is $$F_x = \frac{\phi_x}{2\pi}.$$

2.1 Step by Step Analysis

After mixing by the mixer, the desired fluorescence signal $y_s(t)$ and the unwanted background fluorescence noise $y_n(t)$ are modulated by the switching signal from the PLL 60, as follows.

The fluorescence desired signal $$x_s(t) = y_s(t)u(t) \quad (10)$$

$$= \begin{cases} A_s \sin(\omega t + \phi_s) & 0 < t < \left(\frac{1}{2} - F_x\right)T \\ -A_s \sin(\omega t + \phi_s) & \left(\frac{1}{2} - F_x\right)T < t < (1 - F_x)T \\ A_s \sin(\omega t + \phi_s) & (1 - F_x)T < t < T \end{cases}$$

The background fluorescence from microfluidic substrate (noise)

$$x_n(t) = y_n(t)u(t) = \begin{cases} A_n \sin(\omega t + \phi_n) & 0 < t < \left(\frac{1}{2} - F_x\right)T \\ -A_n \sin(\omega t + \phi_n) & \left(\frac{1}{2} - F_x\right)T < t < (1 - F_x)T \\ A_n \sin(\omega t + \phi_n) & (1 - F_x)T < t < T \end{cases} \quad (11)$$

Hence, the output of the mixer is:

$$x_{total}(t) = x_s(t) + x_n(t)$$

The phase difference between signal and noise is $\Delta\phi = \phi_n - \phi_s$.

Frequency, $f_{mod} = \omega/2\pi$; and Period, $T = 1/f$

The DC voltage for the desired signal after integration, $V_s$, is calculated as follows $$V_s = \int_0^T y_s(t) \cdot u(t) \cdot dt$$

$$= \int_0^T [A_s \sin(\omega t + \phi_s)] \cdot u(t) \cdot dt$$

$$V_s = \int_0^{\left(\frac{1}{2} - F_x\right)T} [A_s \sin(\omega t + \phi_s)] \cdot dt +$$

$$\int_{\left(\frac{1}{2} - F_x\right)T}^{(1 - F_x)T} -[A_s \sin(\omega t + \phi_s)] \cdot dt +$$

$$\int_{(1 - F_x)T}^T [A_s \sin(\omega t + \phi_s)] \cdot dt$$

$$= \frac{A_s}{\omega} \cdot [-\cos(\omega t + \phi_s)|_0^{T\left(\frac{1}{2} - F_x\right)} +$$

$$\cos(\omega t + \phi_s)|_{T\left(\frac{1}{2} - F_x\right)}^{T(1 - F_x)} -$$

$$\cos(\omega t + \phi_s)|_{T(1 - F_x)}^T]$$

-continued $$V_s = \frac{A_s}{\omega}\left\{-\cos\left[2\pi\left(\frac{1}{2}-F_x\right)+\phi_s\right]+\cos(\phi_s)+\right.$$
$$\cos[2\pi(1-F_x)+\phi_s]-\cos\left[2\pi\left(\frac{1}{2}-F_x\right)\right]-$$
$$\left.\cos[2\pi+\phi_s]+\cos[2\pi(1-F_x)+\phi_s]\right\}$$
$$=\frac{2A_s}{\omega}\left\{-\cos\left[2\pi\left(\frac{1}{2}-F_x\right)+\phi_s\right]+\cos[2\pi(1-F_x)+\phi_s]\right\}$$

Hence, the DC fluorescence desired signal is $$V_s = \frac{4A_s}{\omega}\cos(\phi_x - \phi_s) \tag{12}$$

And the DC voltage of the unwanted signal $V_n$, noise due to background fluorescence of the substrate, is calculated as follows:

$$V_n = \int_0^T y_n(t) \cdot u(t) \cdot dt \tag{13}$$
$$= \int_0^T [A_n\sin(\omega t + \phi_n)] \cdot u(t) \cdot dt$$
$$V_n = \int_0^{(\frac{1}{2}-F_x)T} [A_n\sin(\omega t + \phi_n)] \cdot dt +$$
$$\int_{(\frac{1}{2}-F_x)T}^{(1-F_x)T} -[A_n\sin(\omega t + \phi_n)] \cdot dt +$$
$$\int_{(1-F_x)T}^{T} [A_n\sin(\omega t + \phi_n)] \cdot dt$$
$$= \frac{A_n}{\omega} \cdot [-\cos(\omega t + \phi_n)|_0^{T(\frac{1}{2}-F_x)} +$$
$$\cos(\omega t + \phi_n)|_{T(\frac{1}{2}-F_x)}^{T(1-F_x)} -$$
$$\cos(\omega t + \phi_n)|_{T(1-F_x)}^{T}]$$
$$V_n = \frac{A_n}{\omega}\left\{-\cos\left[2\pi\left(\frac{1}{2}-F_x\right)+\phi_n\right]+\cos(\phi_n)+\right.$$
$$\cos[2\pi(1-F_x)+\phi_n]-\cos\left[2\pi\left(\frac{1}{2}-F_x\right)+\phi_n\right]-$$
$$\left.\cos[2\pi+\phi_n]+\cos[2\pi(1-F_x)+\phi_n]\right\}$$
$$=\frac{2A_n}{\omega}\left\{-\cos\left[2\pi\left(\frac{1}{2}-F_x\right)+\phi_n\right]+\cos[2\pi(1-F_x)+\phi_n]\right\}$$
$$V_n = \frac{4A_n}{\omega}\cos(\phi_x - \phi_n)$$

The total DC signal of the fluorescence desired signal, and unwanted noise at the output of integration system 90 illustrated in FIG. 4 is:

$$V_{out} = (12) + (13) \tag{14}$$
$$= V_s + V_n$$
$$V_{out} = \frac{4A_s}{\omega}\cos(\phi_x - \phi_s) + \frac{4A_n}{\omega}\cos(\phi_x - \phi_n)$$

2.2 The Ideal Case: $y_n(t)$ is completely eliminated and $y_s(t)$ is Maximized

To completely eliminate $y_n(t)$, the following must be made:

$$\frac{4A_n}{\omega}\cos(\phi_x - \phi_n) = 0 \Rightarrow \phi_x - \phi_n = k_1\pi + \frac{\pi}{2} \tag{15}$$
$$(k_1 = 0, \pm 1, \pm 2 \ldots)$$

To maximize the desired signal $y_s(t)$, make the $$\cos(\phi_x-\phi_s)=\pm 1 \Rightarrow \phi_x-\phi_s=k_2\pi \; (k_2=0, \pm 1, \pm 2 \ldots) \tag{16}$$

Thus, from equations (15) and (16), to completely eliminate the noise and maximize the desired signal, the switching signal, u(t), and modulation frequency, $f_{mod}$, are generated and adjusted such that u(t) is in phase with the desired signal $y_s(t)$, and $y_s(t)$ has a 90° phase difference from the noise signal $y_n(t)$.

Suppose, ideal requirements are selected as follows:

$$\begin{cases} \phi_s = \phi_x = 0 \\ \Delta\phi = \phi_n - \phi_s = \frac{\pi}{2} \end{cases} \tag{17}$$

Figure 6:
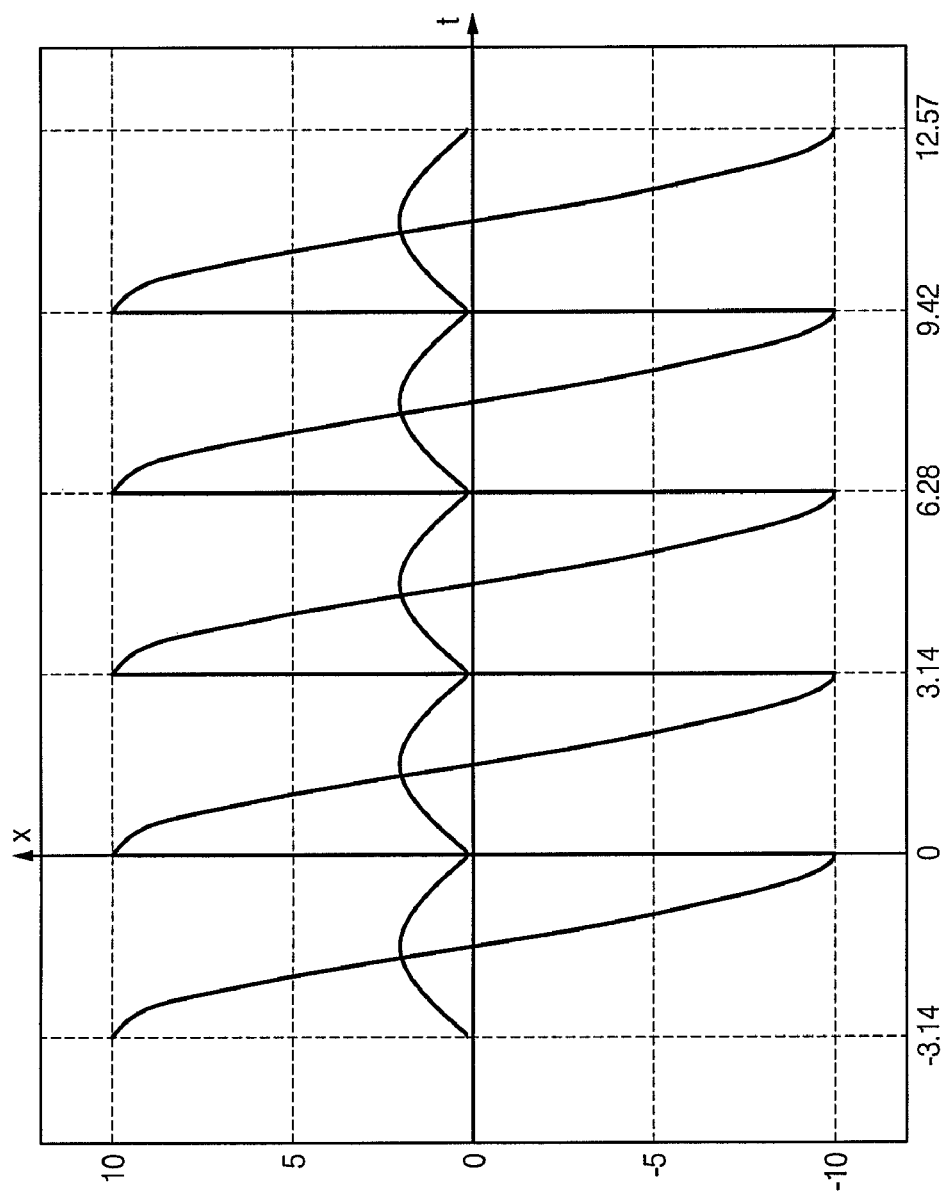
FIG. 6 is an illustration of the waveform at the output of mixer if the condition is ideal.

FIG. 6 show where u(t) is in phase with the desired signal $y_s(t)$, and $y_s(t)$ is 90° deviated from the noise signal $y_n(t)$. So that the waveform after the mixer should be as shown in FIG. 6 the DC voltage at the output of the integration system 90 is:

$$V_0 = \frac{4A_s}{\omega} \tag{18}$$

However, the ideal case may not be achievable due to current technical limitations or other constraints. For an example, due to very short lifetime difference between the fluorophore fluorescence lifetime and the microfluidic substrate auto-fluorescence lifetime which may be in order of nm, a high frequency modulation, in order of GHz, is required to achieve the ideal case. If an LED is used as the excitation source, which cannot be modulated at such a high frequency, the ideal condition above is not possible. Although the ideal condition may not be achievable, the technique is still useful to minimize the effect of the unwanted background signal from the substrate. Hence, the technique remains applicable for detecting very low concentrations of fluorescently labeled samples in a high fluorescence background microfluidic substrate both for ideal and non-ideal cases. Below is an analysis based on the general case, the ideal and non-ideal cases.

2.3 General Case

Suppose for simplification, that $\phi_s=0$, so the phase difference between signal and noise is $\Delta\phi=\phi_n$. For general cases, $\phi_x$ and $\phi_n$ are arbitrary, so that the DC voltage for signal and noise are:

$$V_s = \frac{4A_s}{\omega}\cos(\phi_x) \tag{19}$$

$$V_n = \frac{4A_n}{\omega}\cos(\phi_x - \phi_n) \tag{20}$$

Equation (20) shows that in order to completely eliminate the noise, $(\phi_x-\phi_n)=90°=\pi/2$ (ideal condition). However, sometimes this condition cannot be achieved due to reasons explained previously. Usually, there is a small offset angle ($\beta$), so that $\phi_x = \phi_n + (\pi/2 + \beta)$. Hence, u(t) has following phase relationship with $\phi_n$, that is, ($\beta$ is small offset angle):

$$\begin{cases} \phi_x \neq 0 \\ \phi_x - \phi_n = \frac{\pi}{2} + \beta \end{cases} \Rightarrow \begin{cases} \phi_x \neq 0 \\ \phi_x = \phi_n + \left(\frac{\pi}{2} + \beta\right) \end{cases}$$

Thus, the DC voltages for signal and noise become, $$V_s = \frac{4A_s}{\omega}\cos\left[\phi_n + \left(\frac{\pi}{2} + \beta\right)\right] \quad (21)$$
$$= -\frac{4A_s}{\omega}\sin(\phi_n + \beta)$$

$$V_n = \frac{4A_n}{\omega}\cos\left[\frac{\pi}{2} + \beta\right] \quad (22)$$
$$= -\frac{4A_n}{\omega}\sin(\beta)$$

Therefore, the output for general cases:

$$V_{out} = \frac{4A_s}{\omega}\sin(\phi_n + \beta) + \frac{4A_n}{\omega}\sin(\beta) \quad (23)$$

And the signal to noise ratio is:

$$\left(\frac{S}{N}\right)_{dB} = 10\log\frac{A_s^2(1+\cos 2\phi_x)}{A_n^2[1+\cos(2\phi_x - 2\phi_n)]} \quad (24)$$

$$= 10\log\frac{A_s^2\left[1+\cos 2\left(\phi_n + \frac{\pi}{2} + \beta\right)\right]}{A_n^2\{1+\cos\left[2\left(\phi_n + \frac{\pi}{2} + \beta\right) - 2\phi_n\right]\}}$$

$$\left(\frac{S}{N}\right)_{dB} = 10\log\frac{A_s^2[1-\cos 2(\phi_n + \beta)]}{A_n^2[1-\cos(2\beta)]}$$

Equations (23 and 24) show that the smaller the $\beta$, the higher the signal to noise ratio $$\left(\frac{S}{N}\right)_{dB}.$$

Hence, to minimize the noise level, $\beta$ has to be made as small as possible. Since $\phi_n$, $\beta$, $\omega$, and $A_n$ are constant parameters in a measurement, equation (23) shows us $V_{out}$ is proportional to $A_s$ which is proportional to the concentration of sample. Hence, $V_{out}$ is proportional to the concentration of sample of interest.

III. Third Embodiment

Using Quadrature Annihilator and Phase-Locked Loop

Figure 7:
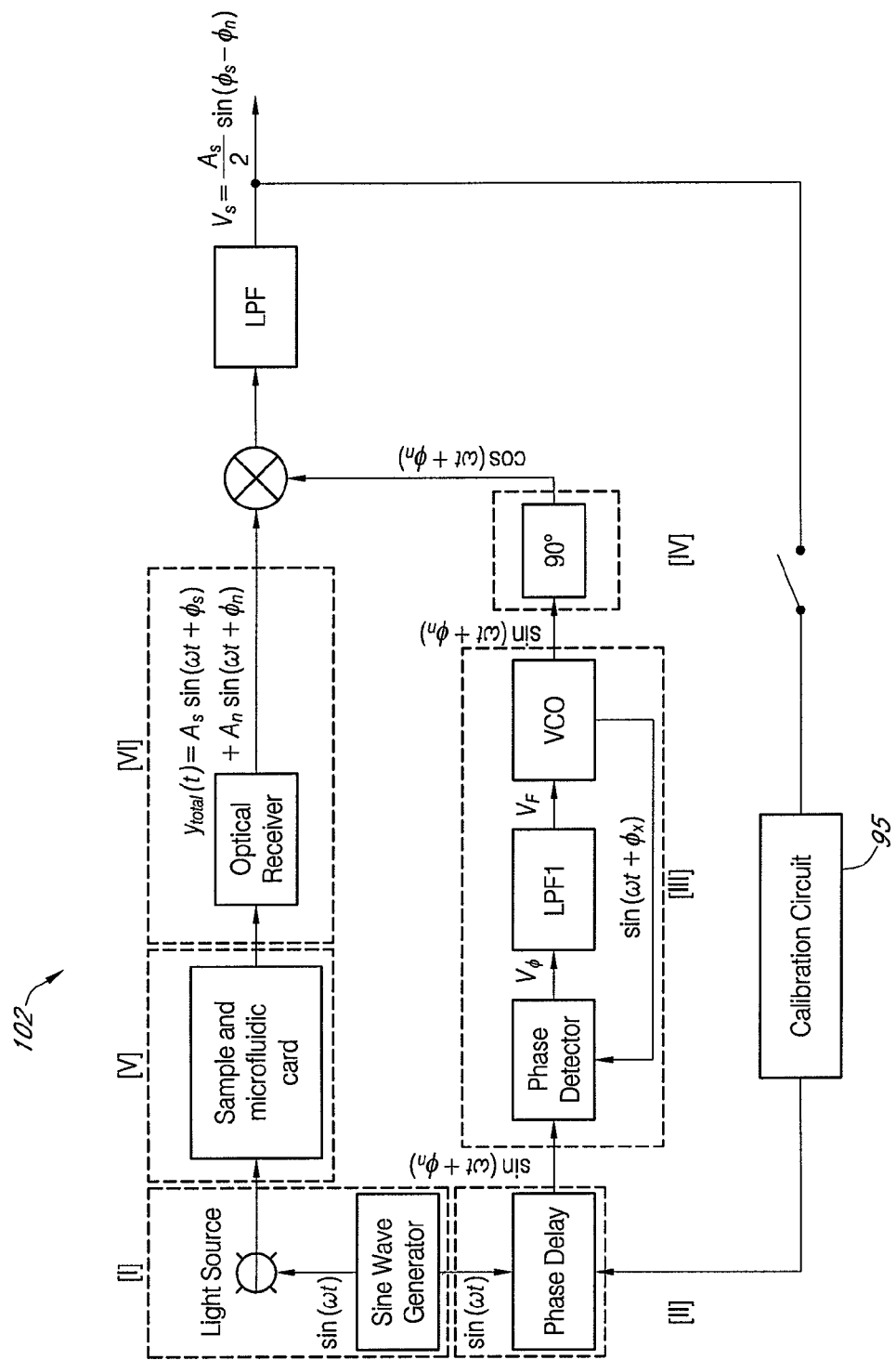
FIG. 7 is a layout of a third embodiment for fluorescence noise elimination.

Referring to FIG. 7, the system 102 is similar to the first embodiment which consists of six main blocks, namely the tunable modulated light source system [I], the phase delay generator [II], the phase-locked loop circuitry [III], the quadrature phase shifter [IV], the sample (sample and microfluidic card) [V], and the optical receiver [VI].

The difference in the third embodiment compared to the first embodiment is that the phase delay is tuned to $\phi_n$, where $\phi_n$ is the phase of the unwanted fluorescence signal, so that the output of the phase delay generator 50 is $\sin(\omega t + \phi_n)$, which is input into the phase-locked loop circuitry in order to ensure the phase is locked. The tuning can be carried out by inserting a same microfluidic card, without the sample, and tuning the phase delay generator 50 so that the output of the low pass filter (LPF) 80 is zero. A calibrator 95 can be incorporated to tune the phase delay generator 50 automatically using the output of the low pass filter 80 as the error signal to the calibrator 95.

The frequency of light source excitation is tuned so that there is a phase difference between desired signal $y_s$ generated by the sample and unwanted signal $y_n$ generated by the microfluidic system 102. Since the phase difference is not required to be 90°, the frequency of excitation is much lower than required for the first embodiment.

3.1 Step by Step Analysis

The signal $y_{total}$ generated by the optical receiver 40 is composed of the signal $y_s$ generated by the sample and unwanted signal $y_n$ generated by the substrate material as follows:

$$y_{total} = y_s + y_n \quad (25)$$
$$= A_s\sin(\omega t + \phi_s) + A_n\sin(\omega t + \phi_n)$$

The output q(t) of the quadrature phase shifter 70 is given by:

$$q(t) = \cos(\omega t + \phi_n) \quad (26)$$

Mixing of (25) and (26) results in:

$$x_q(t) = y_{total}(t) \times q(t) \quad (27)$$
$$= [A_s\sin(\omega t + \phi_s) + A_n\sin(\omega t + \phi_n)] \times \cos(\omega t + \phi_n)$$
$$= A_s\sin(\omega t + \phi_s)\cos(\omega t + \phi_n) + A_n\sin(\omega t + \phi_n)$$
$$\cos(\omega t + \phi_n)$$
$$= \frac{A_s}{2}\sin(\phi_s - \phi_n) + \frac{A_s}{2}\sin(2\omega t + \phi_s + \phi_n) + \frac{A_n}{2}$$
$$\sin(2\omega t + 2\phi_n)$$

There is a DC component and also AC components in equation (27). Suppose the AC components are filtered off using a low pass filter, only the DC component, which is the desired component $V_s$, is left given by:

$$V_s = \frac{A_s}{2}\sin(\phi_s - \phi_n) \quad (28)$$

For a fixed frequency of light source modulation, the phase difference ($\phi_s - \phi_n$) is a constant. Hence the desired component $V_s$ depends only on amplitude $A_s$ which is proportional to the concentration of the labeled sample. As a result, the magnitude of DC level of $V_s$ is proportional to the concentration of sample. Furthermore, the desired component $V_s$ is zero when an identical microfluidic card without a sample is excited by the modulated light source 10. This is used to tune the phase delay generator 50 automatically by incorporating a calibrator 95 to tune the phase delay generator 50 to lock onto the phase of the unwanted signal $y_n$ using $V_s$ as the error signal to the calibrator 95. The phase of the phase delay generator 50 is then fixed by disconnecting the calibrator 95 from the phase delay generator 50 after successful calibration. The testing of an identical microfluidic card with a sample then proceeds with the phase-locked loop locked to the phase of the unwanted signal $y_n$.

Equation (28) shows that this technique is able to eliminate the noise due to auto-fluorescence of microfluidic substrate. The technique is also applicable to eliminate noise $y_g$ given by:

$$y_g = A_0 + A_n \sin(\omega t + \phi_n) + \sum_{k=2}^{\infty} \alpha_k \sin(k\omega t + \phi_k) \qquad (29)$$

The coefficients $\alpha_k$ and the phases $\phi_k$ for $k=2, \ldots, \infty$ of the unwanted signal $y_g$ can be unknown because mixing (26) with components of $y_g$ in equation (29) results in $$\alpha_k \sin(k\omega t + \phi_k) \cos(\omega t + \phi_n) = \qquad (30)$$
$$\frac{\alpha_k}{2} [\sin((k+1)\omega t + \phi_k + \phi_n) + \sin((k-1)\omega t + \phi_k - \phi_n)]$$

The resultant signal in equation (30) and $A_0 \cos(\omega t + \phi_n)$ is filtered out using the same low pass filter. The tuning of the phase delay generator 50 is still required in order to lock the fundamental phase of the unwanted signal $y_g$ so that the phase-locked loop and the quadrature phase shifter 70 generate the required annihilator signal $\cos(\omega t + \phi_n)$. The same calibrator 95 may be used to tune the phase delay generator 50 for the unwanted signal $y_g$.

The Fourth Embodiment

Using Quadrature Demodulator and Phase-Locked Loop

Figure 8:
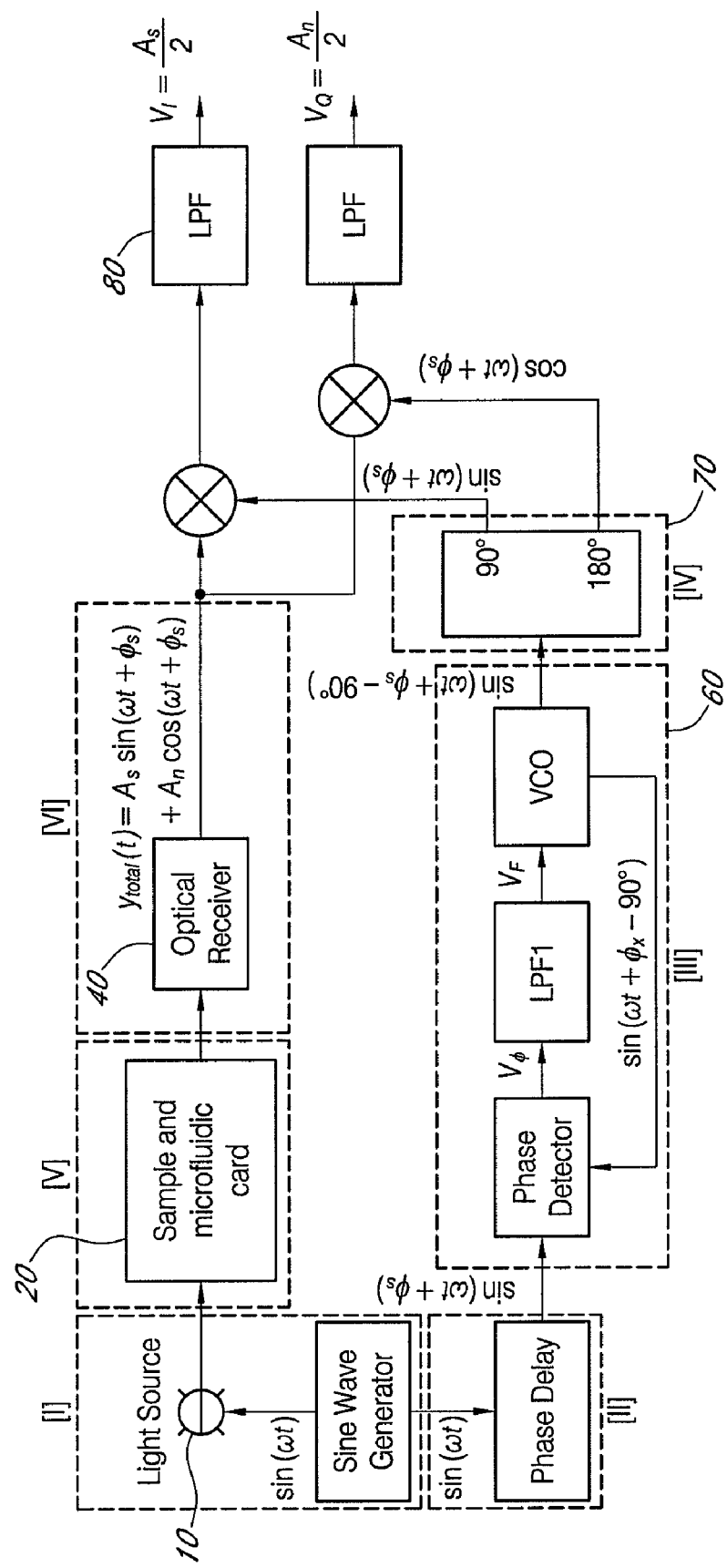
FIG. 8 is an illustration of a fourth embodiment for fluorescence noise elimination.

This embodiment is almost the same as that of the first embodiment. The output of phase lock loop 60 is 90 degree out of phase with the input signal. In order to get the same output, as proposed in the first embodiment, another 90 degree phase shift should be added in quadrature demodulator 70, as shown in FIG. 8.

4.1 Step by Step Analysis

This is substantially the same as for the first embodiment. After the optical receiver 70, the signal generated by the sample and microfluidic card 20 is:

$$y_{total} = y_s + y_n \qquad (10)$$
$$= A_s \sin(\omega t + \phi_s) + A_n \cos(\omega t + \phi_s)$$

The output of the PLL 60 is:

$$V_{PLL} = \sin(\omega t + \phi_s - 90°) \qquad (11)$$

It is fed into the quadrature phase shifter 70, resulting in signals (4) and (5), respectively. Equations (6) and (7) are applied for mixing the output of optical receiver 40 and the two outputs of quadrature phase shifter 70 respectively. The fluorescence signal (8) and unwanted noise signal (9) can be obtained after passing through respective low pass filters.

V. The Fifth Embodiment

Using Only Quadrature Demodulator

Figure 9:
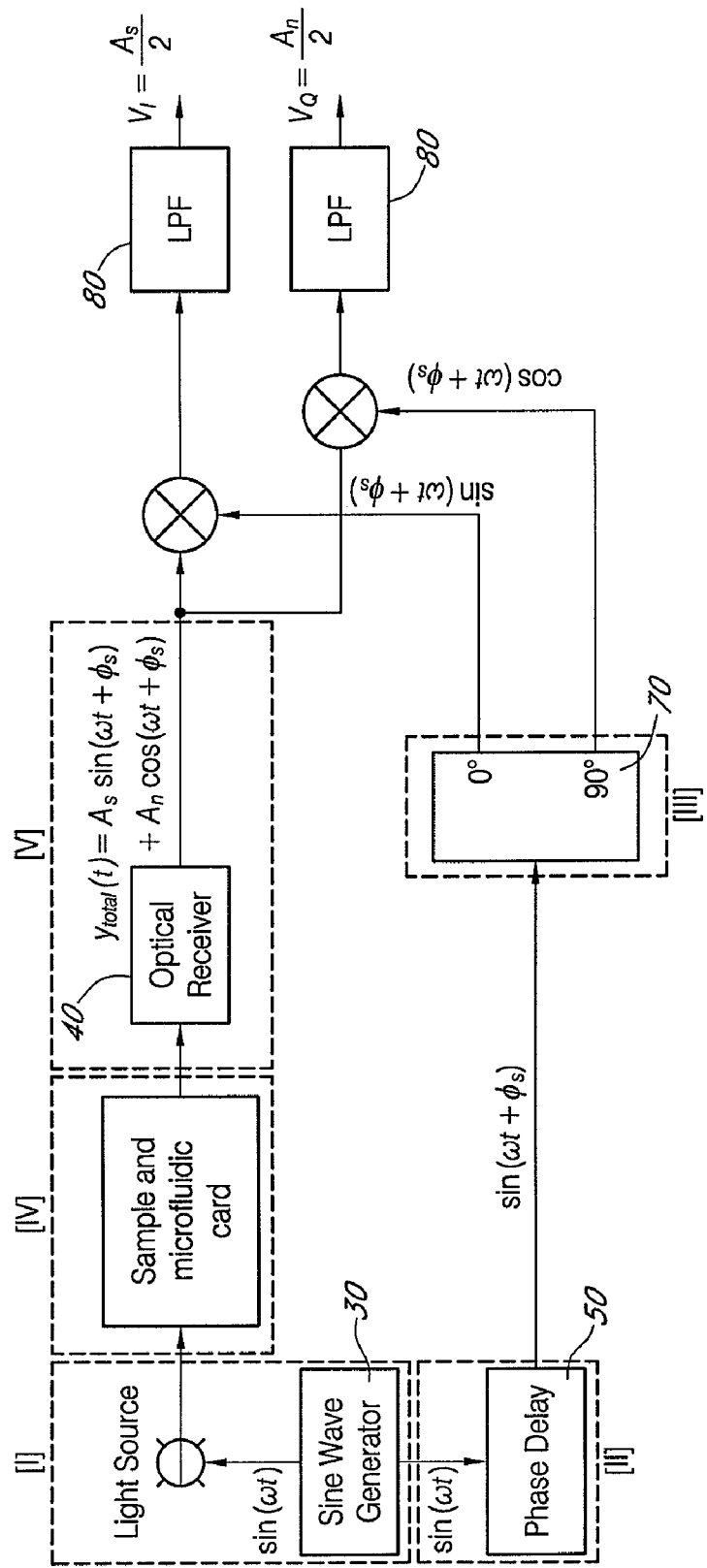
FIG. 9 is an illustration of a fifth embodiment for fluorescence noise elimination.

Phase shift of the signals received from the substrate and the sample depend on the fluorescence life time and modulation frequency. The phase locked loop 60 can be removed in this embodiment. Assuming that the signal from the sine wave generator 30 is stable and controlled in relation to, amongst others, phase and frequency, The phase delay can be turned to $\phi_s$, where $\phi_s$ is the phase of the wanted fluorescence signal, so that the output of phase delay generator so is $\sin(\omega t + \phi_s)$, which will be fed into the quadrature phase shifter 70 and results in two quadrature signals. The two signals are then mixed with output of the optical receiver 40, to give the desired DC signal after the low pass filter 80, as shown in FIG. 9.

The Sixth Embodiment

Using Quadrature Annihilator and Phase-Locked Loop

Figure 10:
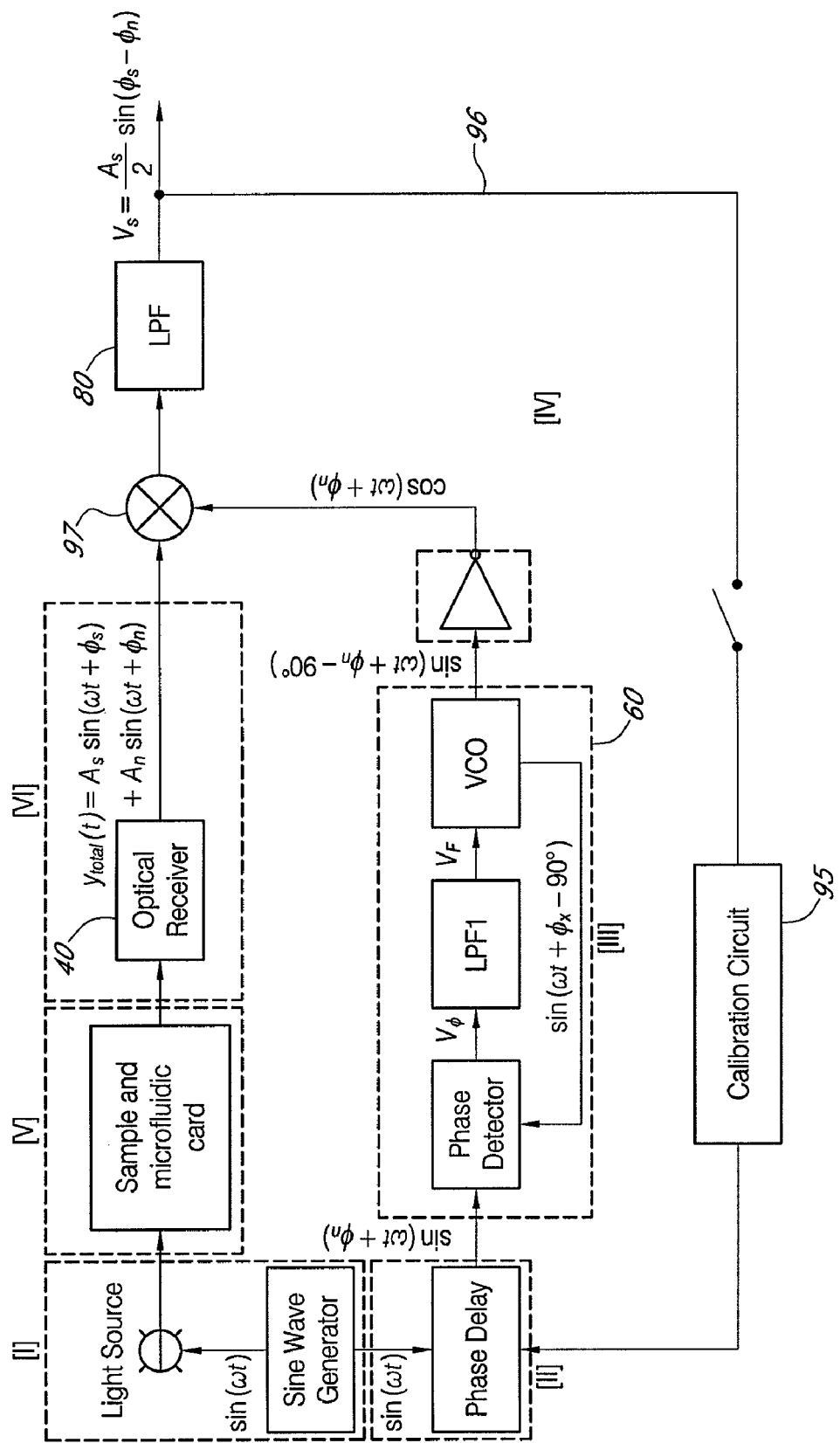
FIG. 10 is an illustration of a sixth embodiment for fluorescence noise elimination.

This embodiment is similar to the third embodiment that consists of 6 main blocks, namely the tunable modulated light source system [I], the phase delay generator [11], the phase-locked loop circuitry [III], the inverter [IV], the sample (sample and microfluidic card) [V], and the optical receiver [VI]. It can also be considered as a special case of the third embodiment where its PLL output is 90 degree out of phase with its input. The system architecture is shown in FIG. 10.

6.1 Step by Step Analysis

The input and output of the phase lock loop 60 are 90 degree out of phase.

$$y_{PLL} = \sin(\omega t + \phi_n - 90°) \qquad (34)$$
$$= -\cos(\omega t + \phi_n)$$

After the inverter (96), the signal becomes $$y_{inverter} = \cos(\omega t + \phi_n);$$

this is the same as that in (25). Thus, the output of the low pass filter 10 is given by $$V_s = \frac{A_s}{2} \sin(\phi_s - \phi_n)$$

6.2 Results

Figure 11:
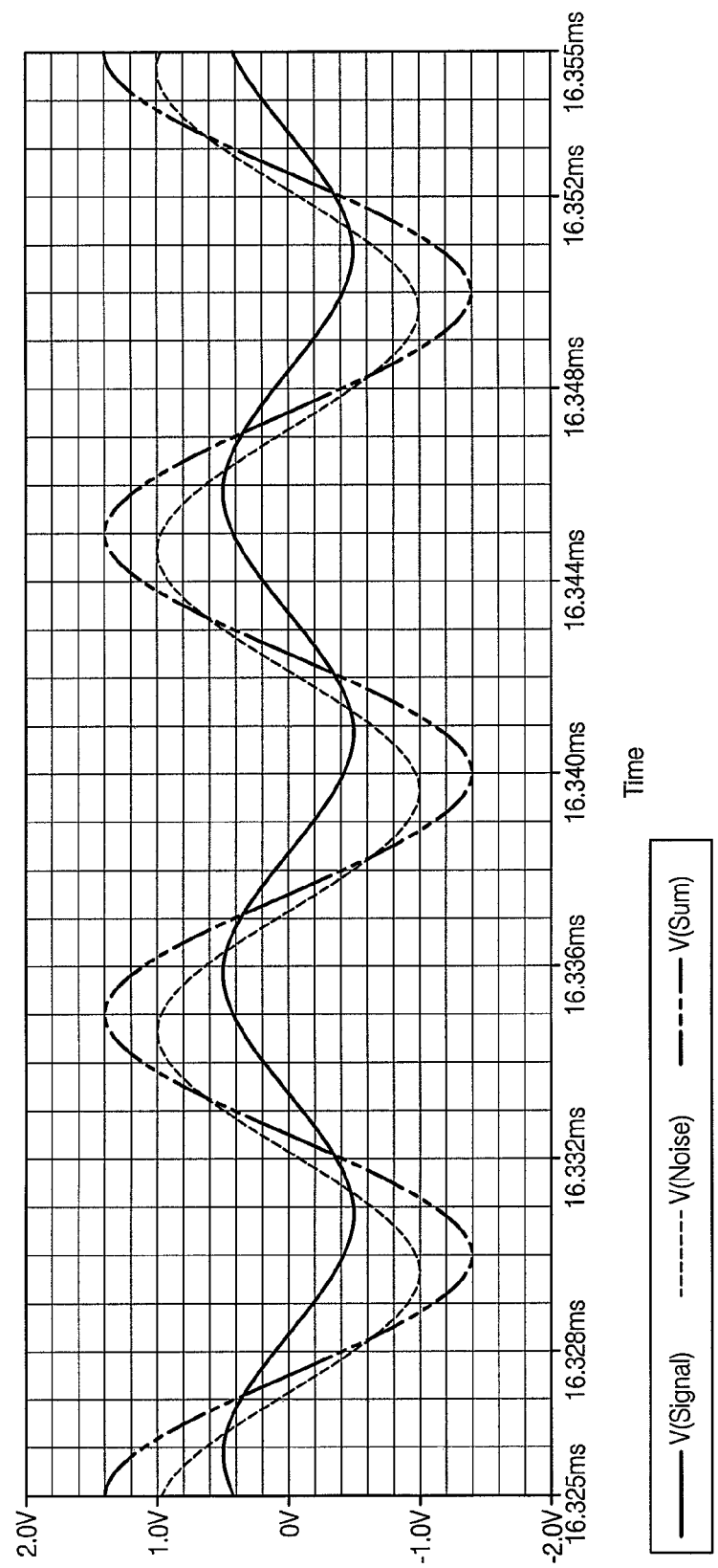
FIG. 11 is a graph of a weak fluorescence signal of interest, high intensity unwanted substrate fluorescence signal, and the sum of both signals.

The conditions are:

Modulation Frequency: f=100 kHz;

Fluorescence signal: $y_s$=0.5 sin $(2\pi*10^5 t + 45.83°)$;

Noise signal: $y_n$=sin $(2\pi*10^5 t + 1.83°)$;

FIG. 11 illustrates the simulation input signal for desired fluorescence signal, noise signal and combination of the two. No offset is added during the initial simulation. The two signals have a phase difference of $\Delta\phi$=44°. The output of the optical receiver is as follows:

$$y_{total} = 0.5 \sin(2\pi*10^5 t + 45.83°) + \sin(2\pi*10^5 t + 1.83°); \qquad (35)$$

Figure 12:
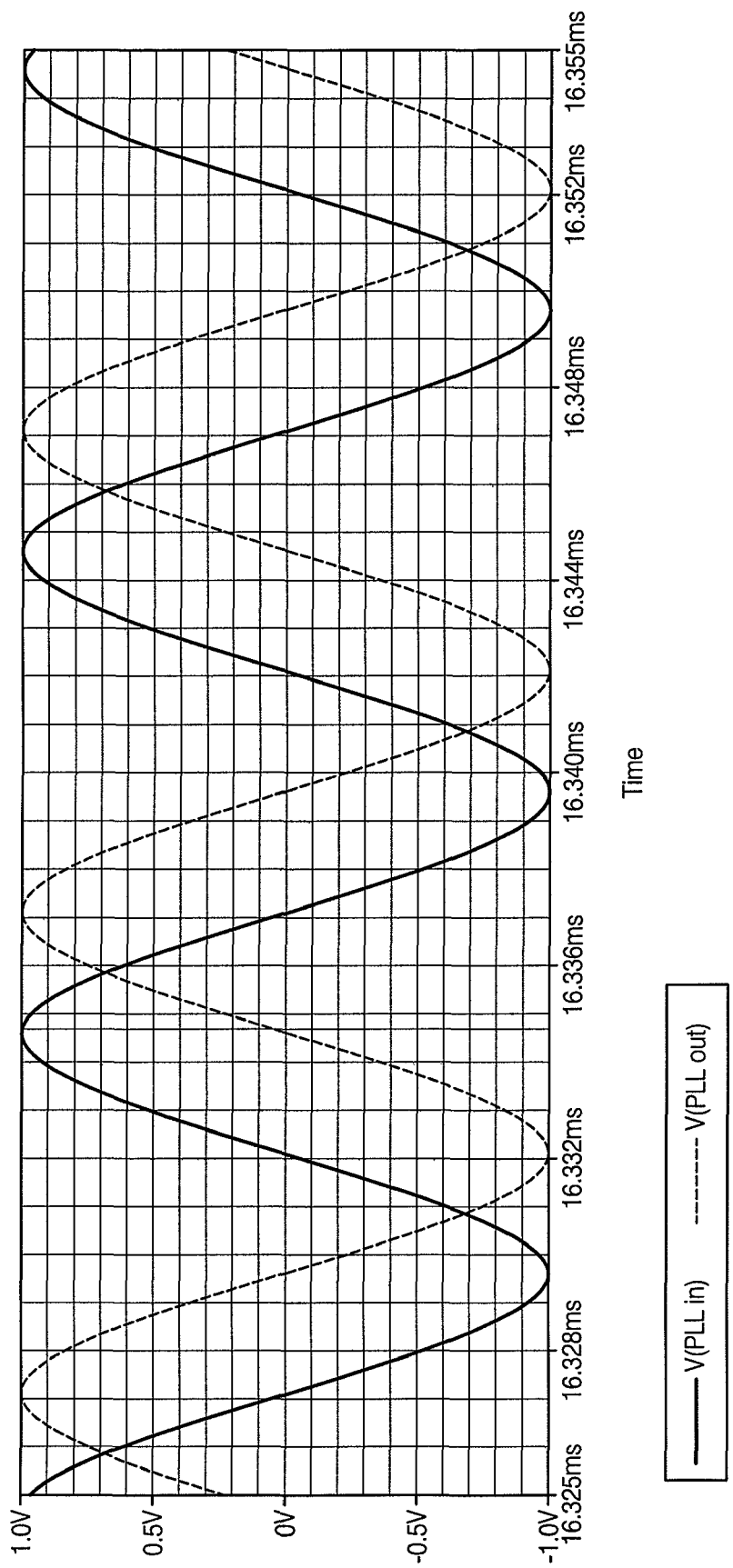
FIG. 12 is a graph input and output signals of the phase locked loop of FIG. 10.

Before any sample is input into the microfluidic card, calibration takes place in order to tune the phase at phase delay (II), as shown in FIG. 10, such that the output of the low pass filter 80 is finally zero. The resultant phase delay in this case is about 45 degrees. This phase is then locked and held by the PLL 60. FIG. 12 shows the response of the PLL. The two signals are 90 degree out of phase. The mathematical derivation for calibration is.

The input signal at output of optical receiver 40:

$y_{total} = y_n = \sin(2\pi*10^5 t + 1.83°)$;

The output of PLL 60 (before calibration is done):

$y_{PLL} = \sin(\omega t + \phi_x - 90)$ where $\phi_x$ is the phase that tuned;

After inverter (96), the signal becomes:

$y_{90} = \cos(2\pi*10^5 t + \phi_x)$

After the multiplication, the resultant signal is:

$$y_{result} = y_{total} \times y_{90}$$
$$= \sin(2\pi*10^5 t + 1.83°) \times \cos(2\pi*10^5 t + \phi_x)$$
$$= \frac{1}{2}[\sin(4\pi*10^5 t + 1.83° + \phi_x) + \sin(1.83° - \phi_x)]$$

So the output signal is:

$$y_{result} = \frac{1}{2}\sin(1.83° - \phi_x) \quad (36)$$

At the end of calibration, $\phi_x = 1.18$ and $y_{result} = 0$. The switch as shown in FIG. 10 is turned off, and samples of interest are added into the microfluidic channel which gives another signal. Thus, the output of the optical receiver becomes the combination of two signals, as shown in equation (35).

The resultant signal at the output of the multiplexer 97 is:

$$y_{result} = [0.5\sin(2\pi*10^5 t + 45.83°) + \sin(2\pi*10^5 t + 1.83°)] \times$$
$$\cos(2\pi*10^5 t + 1.83)$$
$$= 0.25\sin(4\pi*10^5 t + 47.66°) + 0.25\sin(44°) +$$
$$0.5\sin(4\pi*10^5 t + 3.66°)$$

And after the LPF 80, the output signal is:

$y_{result} = 0.25 \sin(44°) = 0.1737$

Figure 13:
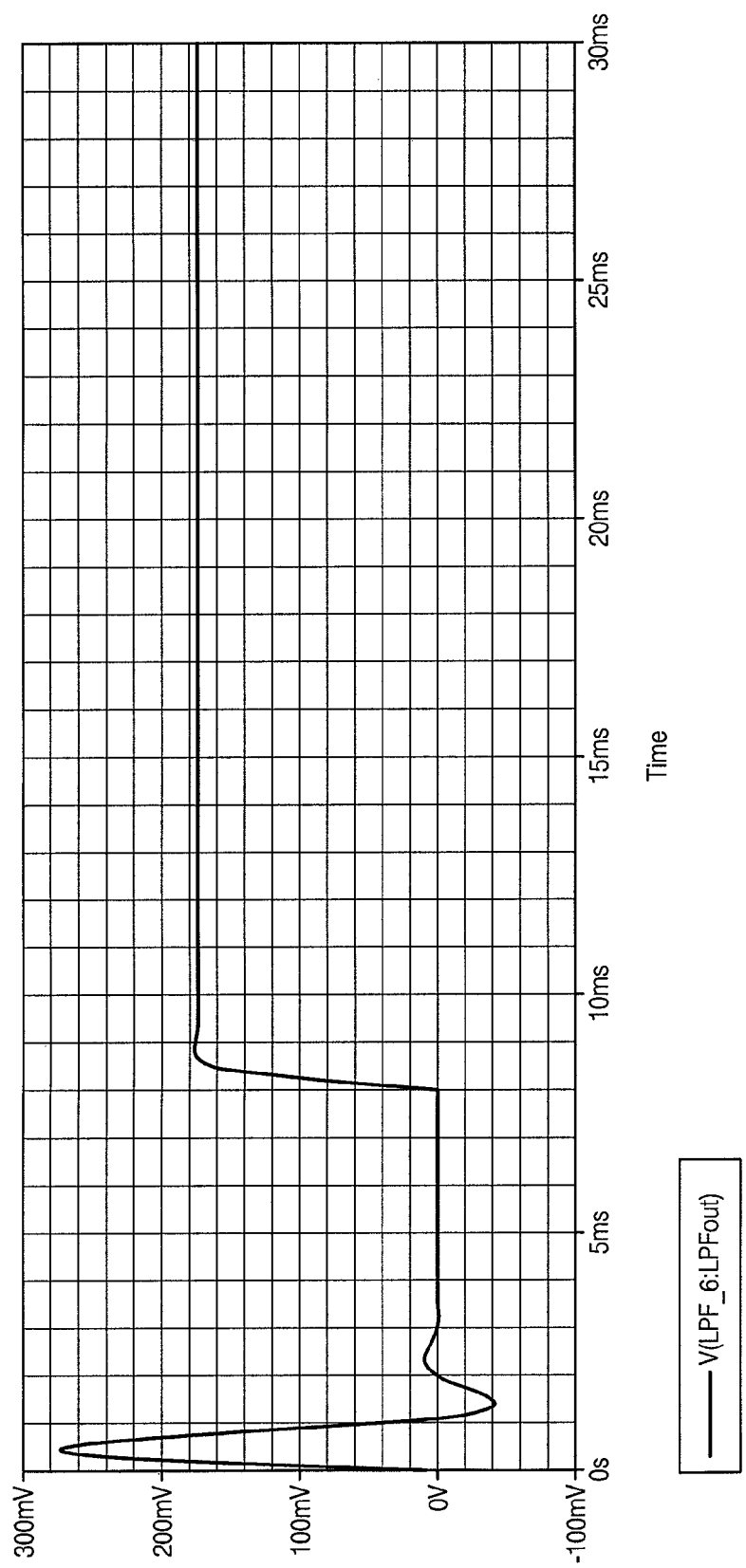
FIG. 13 is a graph of the output of the low pass filter of FIG. 10.

As shown in the FIG. 13, the result corresponds to the derivation.

Figure 14:
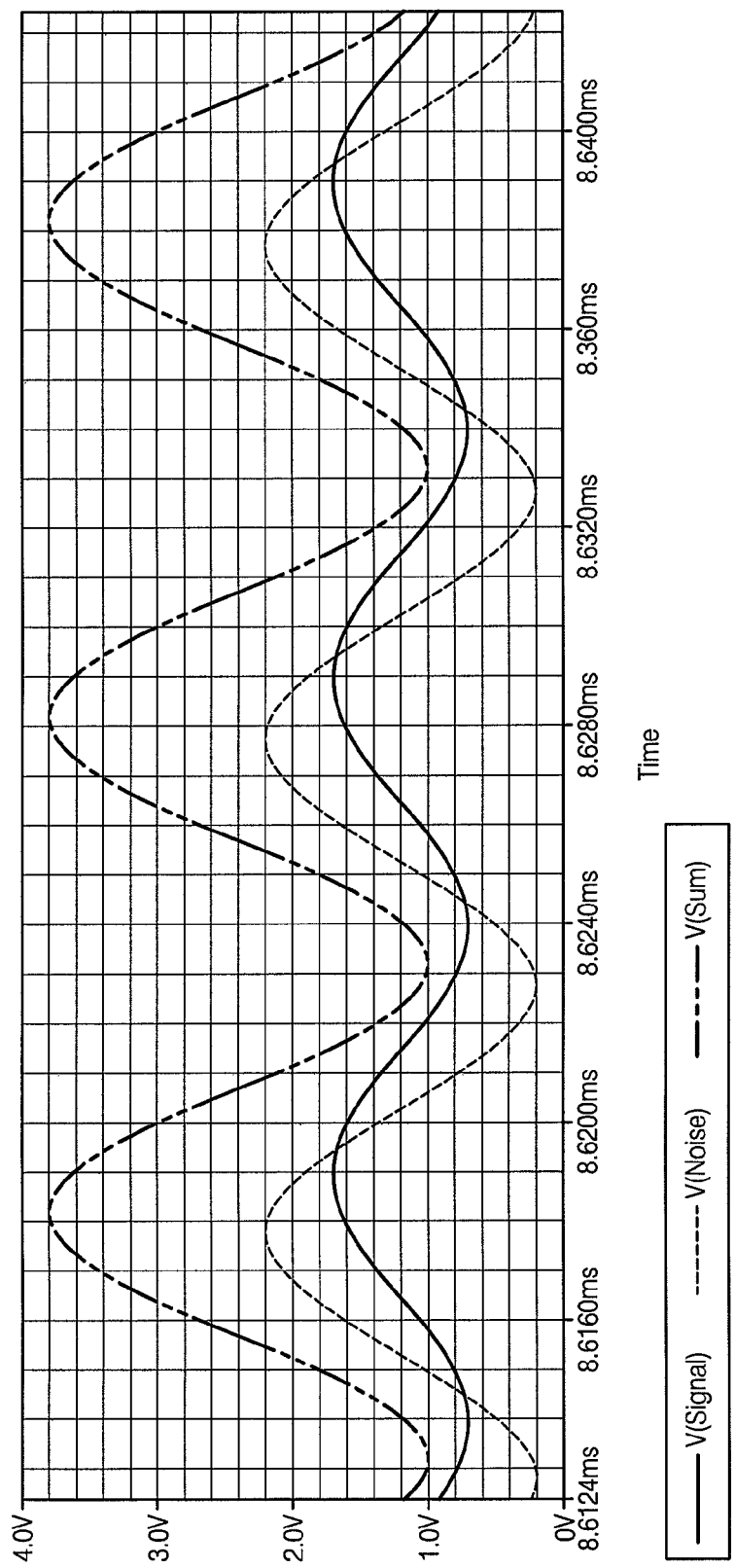
FIG. 14 is a graph corresponding to FIG. 11.

Offset appears at the output of optical receiver 40. It is also needed for biasing the electronic components. Offset is added without changing any other parameters:

Modulation Frequency: f=100 kHz;

Fluorescence signal: $y_s = 0.5 \sin(2\pi*10^5 t + 45.83°) + 1.2$;

Noise signal: $y_n = \sin(2\pi*10^5 t + 1.83°) + 1.2$;

FIG. 14 illustrates the input fluorescence and noise signals, as well as the sum of these two signals. Offset voltage is set to 1.2 V for each of the input signals, resulting following signal at the output of optical receiver.

$$y_{total} = y_s + y_n \quad (36)$$
$$= 0.5\sin(2\pi*10^5 t + 45.83°) + 1.2 +$$
$$\sin(2\pi*10^5 t + 1.83°) + 1.2$$
$$= 0.5\sin(2\pi*10^5 t + 45.83°) + \sin(2\pi*10^5 t + 1.83°) + 2.4$$

Similarly, calibration takes place before pumping any sample. The input signal is:

$y_{total} = y_n = \sin(2\pi*10^5 t + 1.83°) + 1.2$;

The output of PLL 60 (before calibration is done):

$y_{PLL} = \sin(\omega t + \phi_x - 90) + 1.2$ where $\phi_x$ is the phase that is tuned.

After the multiplication, the resultant signal is:

$$y_{result} = y_{total} \times y_{90}$$
$$= [\sin(2\pi*10^5 t + 1.83°) + 1.2] \times [\cos(2\pi*10^5 t + \phi_x) + 1.2]$$
$$= \frac{1}{2}[\sin(4\pi*10^5 t + 1.83° + \phi_x) + \sin(1.83° - \phi_x)] + 1.2 \times$$
$$\sin(2\pi*10^5 t + 1.83°) + 1.2 \times \cos(2\pi*10^5 t + \phi_x) + 1.44$$

After LPF 80, the high frequency aspect is filtered, and results in:

$$y_{result} = \frac{1}{2}\sin(1.83° - \phi_x) + 1.44 \quad (37)$$

Figure 15:
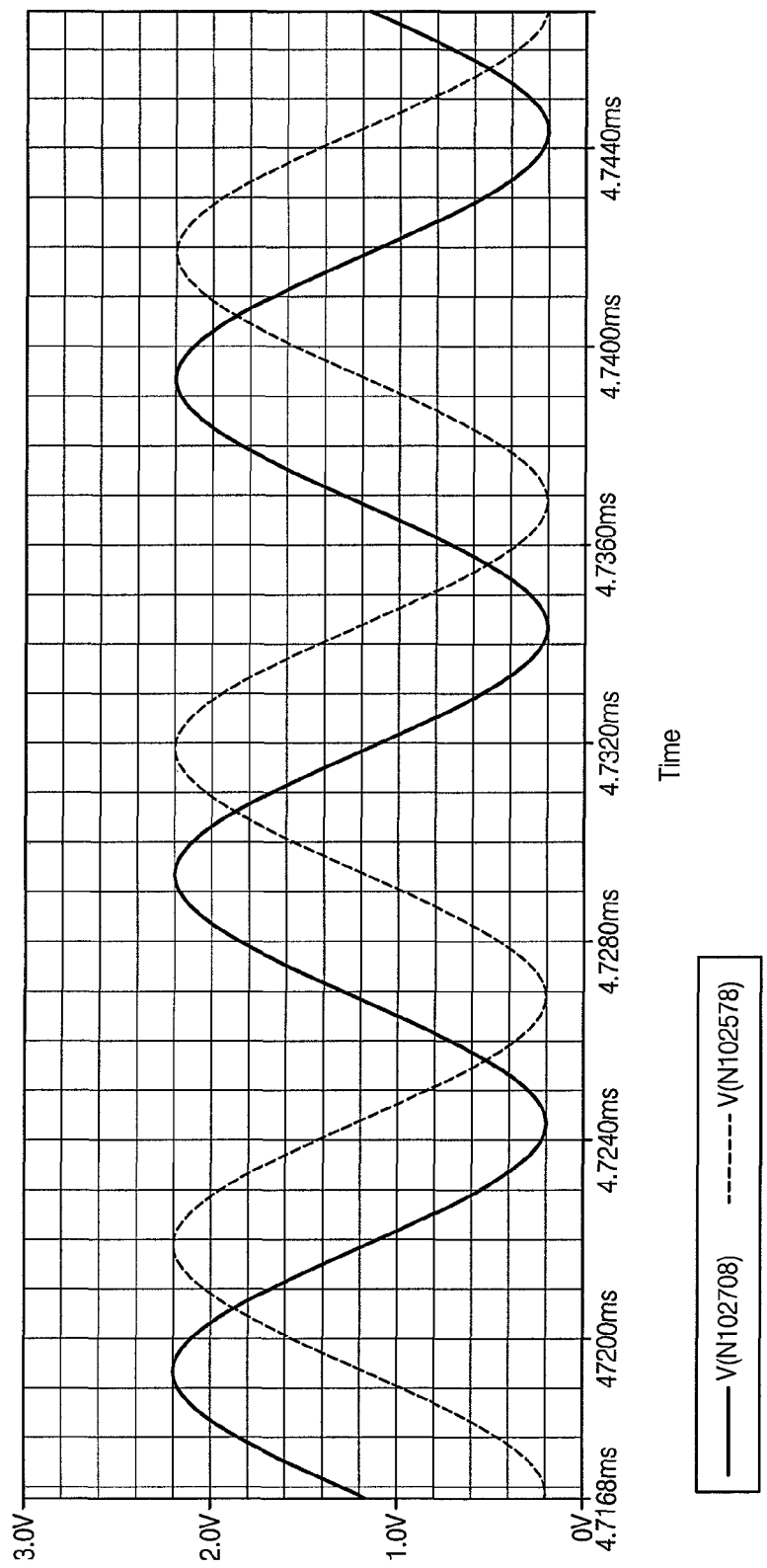
FIG. 15 is a graph corresponding to FIG. 13.

At the end of calibration, $\phi_x = 1.18$ and $y_{result} = 1.44$. FIG. 15 shows the PLL 60 response when calibration is complete. The input and output of PLL 60 is 90 degree out of phase, and have a DC offset of 1.2 V.

After pumping the samples, the signal becomes the mixture of the two signals, as shown in (36). Thus, $$y_{result} = [0.5\sin(2\pi*10^5 t + 45.83°) + \sin(2\pi*10^5 t + 1.83°) + 2.4] \times$$
$$[\cos(2\pi*10^5 t + 1.83) + 1.2]$$
$$= [0.25\sin(4\pi*10^5 t + 47.66°) + 0.25\sin(44°) +$$
$$0.5\sin(4\pi*10^5 t + 3.66°)] + 1.2 \times [0.5\sin(2\pi*10^5 t +$$
$$45.83°) + \sin(2\pi*10^5 t + 1.83°)] + 2.4 \times \cos(2\pi*10^5 t +$$
$$1.83) + 2.88$$

And after the LPF 80, the output signal is:

$y_{result} = 0.25 \sin(44°) + 2.88 = 3.054$

Figure 16:
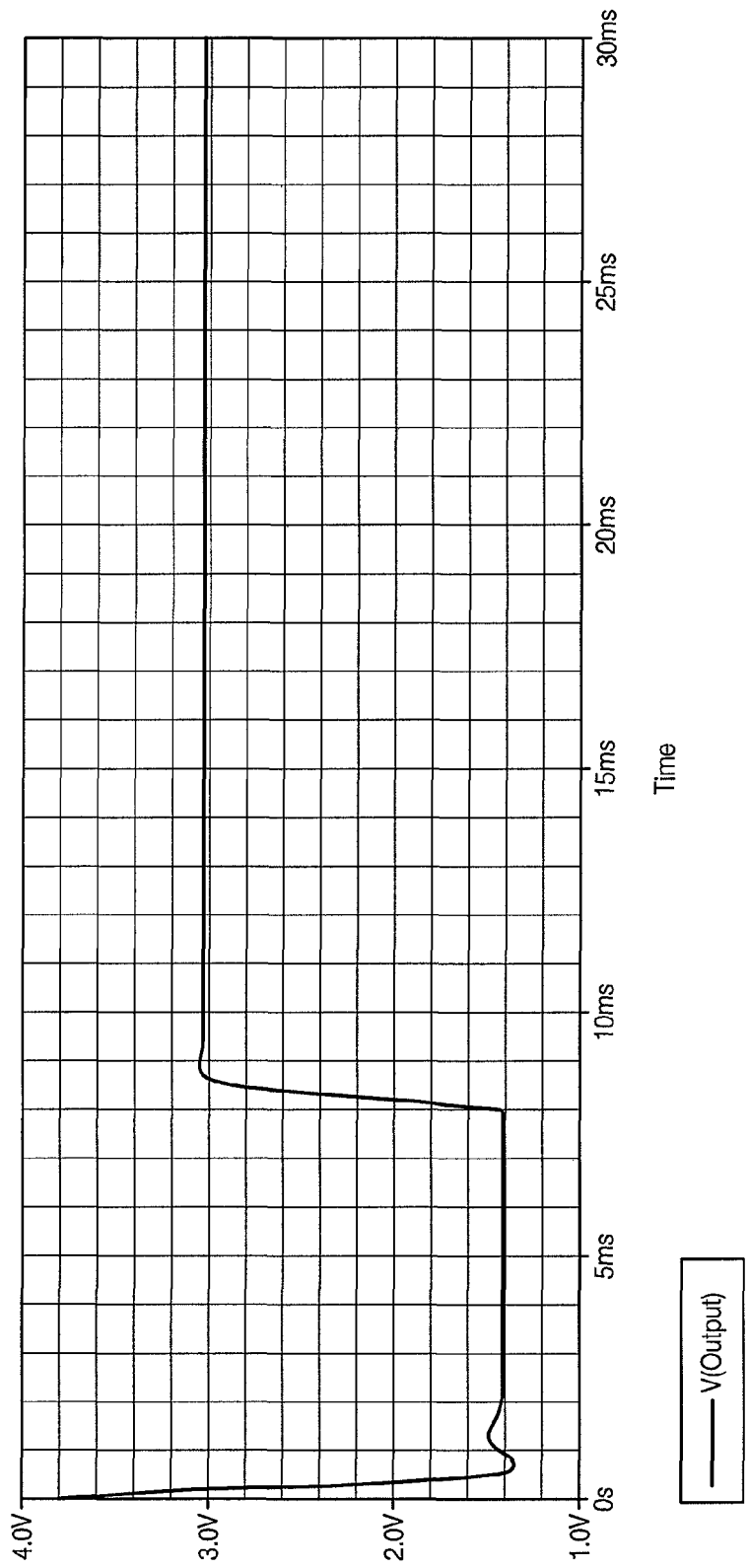
FIG. 16 is a graph corresponding to FIG. 14.

As shown in FIG. 16, the simulation result corresponds to the theoretical analysis. The output signal has a linear relationship with fluorescence intensity and the background noise has been eliminated.

The Seventh Embodiment

Using Only Quadrature Annihilator

Figure 17:
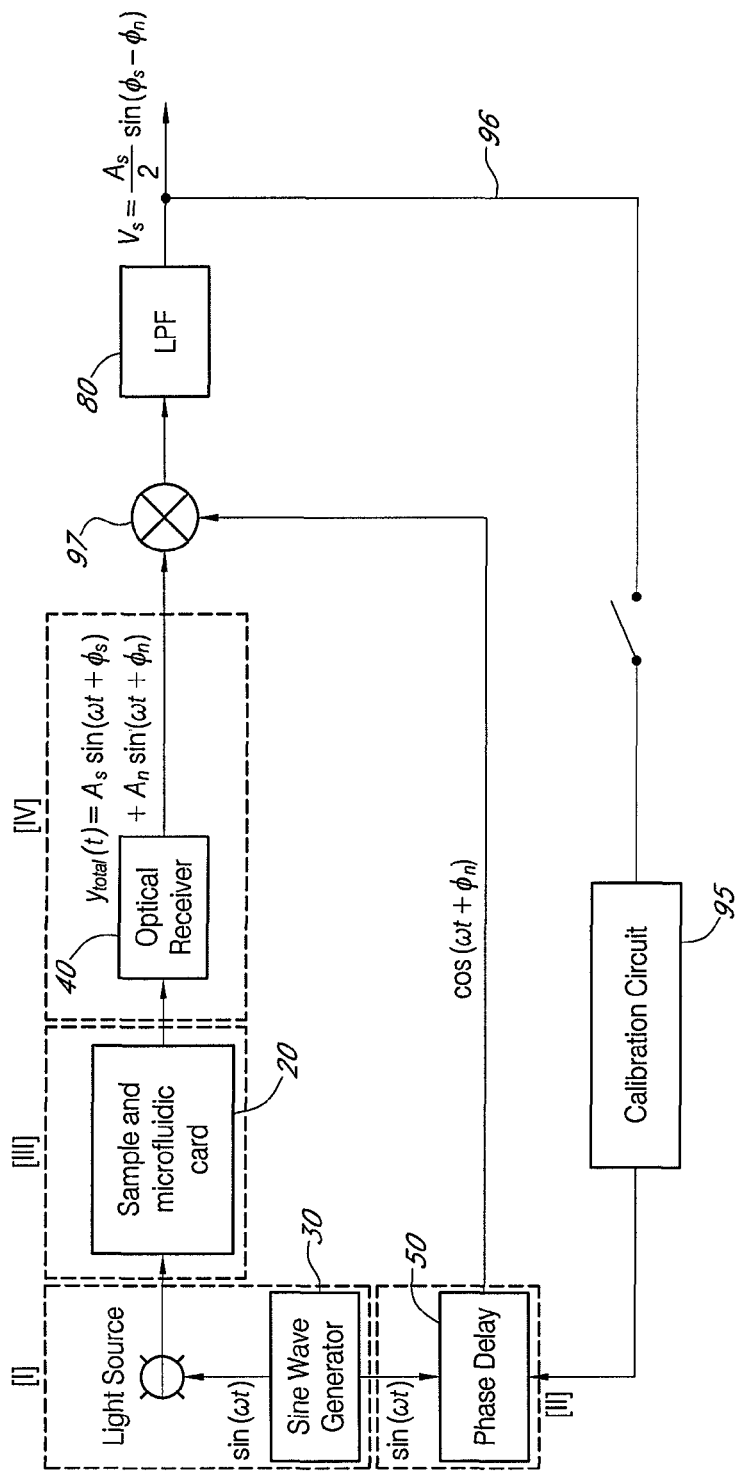
FIG. 17 is an illustration of a seventh embodiment for fluorescence noise elimination.

This is another special case of the third embodiment, and is relevant when the signal after the sine wave generator 30 is stable and well controlled in so far as, for example, phase and frequency. The phase shift is tuned to be ($\phi_n$+90°) by using the calibrator 95. Thus, the output of the phase delay can be directly fed into the mixer 97, and after the LPF 80, the desired DC value can be obtained. The system architecture is shown in FIG. 17.

7.1 Step by Step Analysis

The signal at the output of the sine wave generator 30 is tuned by ($\phi_n$+90°), thus, $$y_{phaes} = \sin(\omega t + \phi_n + 90°)$$
$$= \cos(\omega t + \phi_n)$$

After calibration, samples are pumped into the microfluidic card 20, and two signals' mixture is produced at the output of the optical receiver 40. The output of the phase delay 50 is directly fed into the mixer 97, and passed through LPF 80 to filter out the high frequency components. The desired DC signal can be obtained. Detail mathematical derivation is the same as that in the third embodiment.

The Eighth Embodiment

Using Only Quadrature Annihilator

Figure 18:
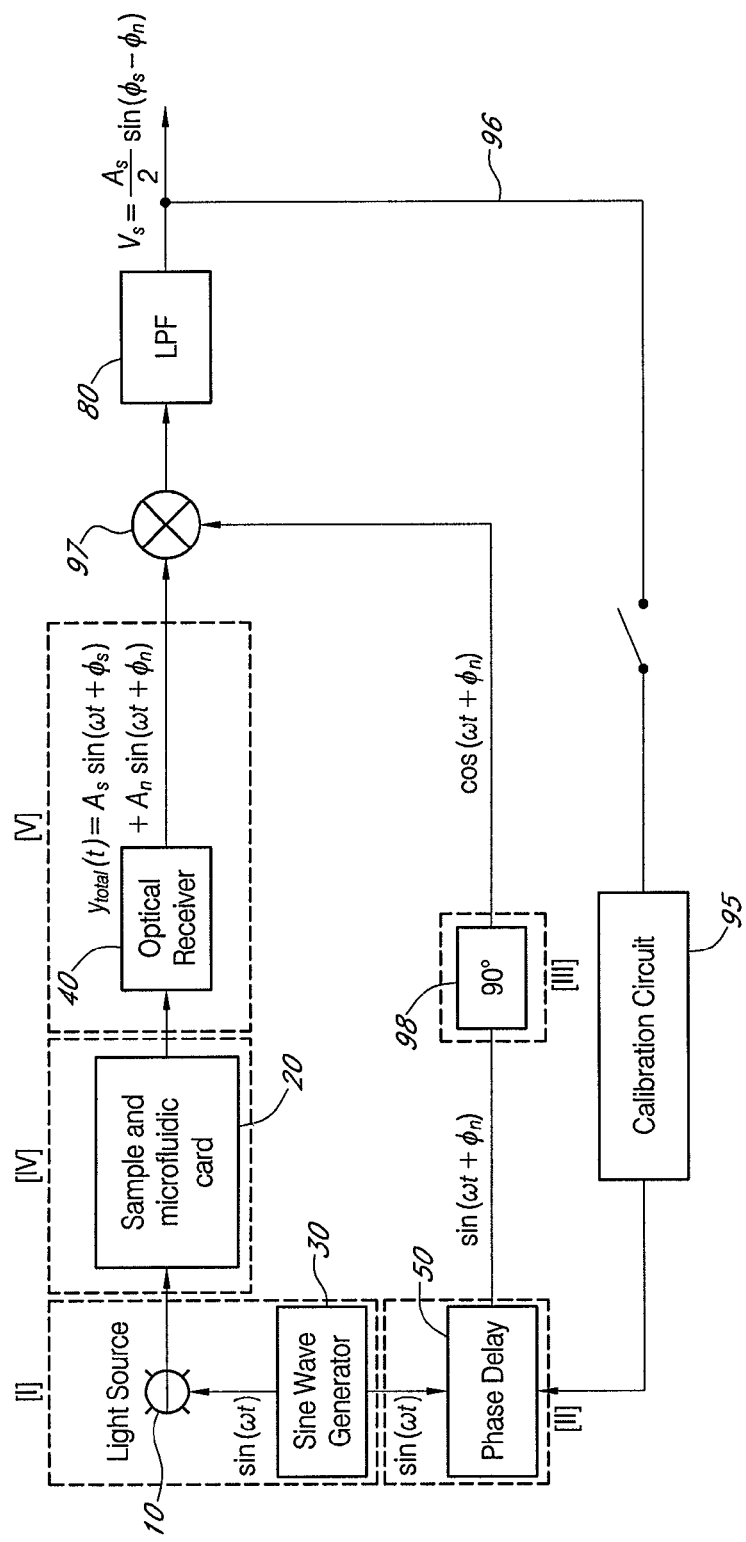
FIG. 18 is an illustration of an eighth embodiment for fluorescence noise elimination.

This scheme is almost the same as that in the seventh embodiment. However, in the seventh embodiment tuning ($\phi_n$+90°) to achieve signal cos ($\omega t+\phi_n$) directly is much more difficult than tuning at $\phi_n$ followed by a 90 degree phase shift. This is an improvement of the seventh embodiment, though one more block (quadrature phase shifter III) 98 is added into the system. The system architecture is shown in FIG. 18.

INDUSTRIAL APPLICABILITY

Because this technique enables the elimination of the noise signal due to the fluorescence background of a substrate by using the difference between the fluorescent emission lifetimes of the fluorescein and the substrate, polymeric materials having high background fluorescence may be used as the substrate to reduce cost, simplify fabrication and increase robustness. Polymeric sheets are relatively cheaper than optical grade glasses and silica wafers, which are presently commonly used as substrate. The substrate may be a microfluidic channel of a microfluidic substrate. In that case the cost of the microfluidic chips can be reduced, and they may be able to considered as consumable items by being disposable cartridges at the point-of-care immunoassay system. As a polymeric microfluidic chip is also relatively robust, it may be suitable for less trained users who are the target of point-of-care diagnosis in distributed-diagnostic and home-healthcare system.

Whilst there has been described in the foregoing description preferred embodiments of the present invention, it will be understood by those skilled in the technology concerned that many variations or modifications in details of design or construction may be made without departing from the present invention.

The invention claimed is:

1. A method for measuring a fluorescent sample on a substrate, the method comprising:
    (a) exciting the fluorescent sample with an exciting light source for the generation of a sample fluorescent optical signal and a substrate fluorescent optical signal;
    (b) substantially eliminating the substrate fluorescent optical signal and leaving the sample fluorescent optical signal; and
    (c) processing the sample fluorescence optical signal, wherein the substantially eliminating the substrate fluorescence signal comprises:
        (i) modulating the frequency of a light source to excite fluorophore of the sample according to a predetermined modulation frequency such that a phase difference between the sample fluorescence optical signal and the substrate fluorescence optical signal is substantially 90 degrees;
        (ii) generating a sine wave signal based on a unity-gain sine wave signal corresponding to the predetermined modulation frequency delayed by the phase of the substrate fluorescence optical signal;
        (iii) mixing the sine wave signal with an acquired signal corresponding to the fluorescence emission of the sample and the substrate, into at least one mixed signal; and
        (iv) filtering the at least one mixed signal to obtain a DC component of the fluorescence signal of the sample; and
        (v) wherein the fluorescence emission of the substrate is filtered and the DC component is proportional to the concentration of the fluorescence signal of the sample.

2. A method as claimed in claim 1, wherein generating a sine wave signal based on a unity-gain sine wave signal further comprises generating a unity-gain square wave of the same frequency as the sample fluorescence optical signal; the unity-gain square wave serving as a switching signal for mixing; and wherein substantially eliminating the substrate fluorescence signal further comprises using the switching signal to modulate the sample fluorescence optical signal and the substrate fluorescence optical signal to create the phase difference between them.

3. A method as claimed in claim 1, wherein: modulating the frequency of a light source further comprises modulating the frequency of the light source before introduction of the sample onto the substrate so as to generate the substrate fluorescence optical signal; and wherein substantially eliminating the substrate fluorescence signal further comprises using the substrate fluorescence optical signal to generate a generated signal which is in phase with the substrate fluorescence optical signal; and introducing the sample onto the substrate and modulating the frequency of the light source to excite the fluorophore of the sample according to a predetermined modulation frequency such that there exists the phase difference between the sample fluorescence optical signal and the substrate fluorescence optical signal.

4. The method according to claim 1, wherein the filtering is low-pass filtering.

5. The method of claim 1, wherein the unity-gain sine wave signal is generated by phase-locked loop ("PLL") circuit.

6. The method of claim 5, wherein the PLL circuit comprises a phase detector to generate an average DC voltage proportional to the phase difference, a low-pass filter to suppress high frequency components generated by the phase detector and a voltage-controlled oscillator to control the voltage-controlled oscillator frequency to oscillate at a frequency identical to the input frequency with a finite phase difference.

7. The method of claim 1, wherein a quadrature phase shifter generates the two sine wave signals which are 90 degrees out of phase with each other.

8. The method of claim 1, wherein the fluorophore label is fluorescein.

9. The method of claim 1, wherein the light source is a 470 nm blue LED with 3460 mcd in intensity.

10. The method of claim 1, wherein the substrate is a microfluidic substrate.

11. The method of claim 1, wherein an optical filter filters off signals with a wavelength outside a range of interest.

12. A method for measuring a fluorescent sample on a substrate, the method comprising:
    (a) modulating the frequency of a light source to excite the fluorophore of the sample according to a predetermined modulation frequency such that the phase difference between the sample fluorescence optical signal and the substrate fluorescence optical signal is substantially 90 degrees;
    (b) generating a sine wave signal based on a unity-gain sine wave signal corresponding to the predetermined modulation frequency delayed by the phase of the substrate fluorescence optical signal;
    (c) mixing the sine wave signal with an acquired signal corresponding to the fluorescence emission of the sample and the substrate, into at least one mixed signal; and
    (d) filtering the at least one mixed signal to obtain a DC component of the fluorescence signal of the sample;
    (e) wherein the fluorescence emission of the substrate is filtered and the DC component is proportional to the concentration of the fluorescence signal of the sample.

13. The method according to claim 12, wherein the acquired signal is acquired by an optical receiver.

14. The method of claim 13, wherein the optical receiver is any one selected from the group consisting of: photodiode, avalanche photodiode, photomultiplier tube and CCD detector.

15. A method for measuring a fluorescent sample on a substrate, the method comprising:
    (a) modulating the frequency of a light source to excite the fluorophore of the sample according to a predetermined modulation frequency;
    (b) generating a unity-gain square wave of the same frequency as a sample fluorescence optical signal; the unity-gain square wave serving as a switching signal for mixing;
    (c) mixing the unity-gain square wave with an acquired signal corresponding to the fluorescence emissions of the sample and the substrate, into at least one mixed signal;
    (d) using the switching signal to modulate the sample fluorescence optical signal and the microfluidic substrate fluorescence optical signal to create a phase difference between them; and
    (e) filtering the at least one mixed signal to obtain a DC component of the fluorescence signal of the sample;
    (f) wherein the fluorescence emission of the substrate is filtered and the DC component is proportional to the concentration of the fluorescence signal of the sample.

16. The method according of claim 15, wherein the unity-gain square wave signal is in phase with the fluorescence signal of the sample.

17. A method for measuring a fluorescent sample on a substrate, the method comprising:
    (a) modulating the frequency of a light source before introduction of the sample onto the substrate so as to generate a substrate fluorescence optical signal;
    (b) using the substrate fluorescence optical signal to generate a generated signal which is in phase with the substrate fluorescence optical signal;
    (c) introducing the sample onto the substrate and modulating the frequency of the light source to excite fluorophore of the sample according to a predetermined modulation frequency such that there exists a phase difference between the sample fluorescence optical signal and the substrate fluorescence optical signal;
    (d) generating a sine wave signal based on a unity-gain sine wave signal corresponding to the predetermined modulation frequency and with a phase difference of 90 degrees with respect to the phase of the generated signal;
    (e) mixing the sine wave signal with an acquired signal corresponding to the fluorescence emission of the sample and the substrate, into at least one mixed signal; and
    (f) filtering the at least one mixed signal to obtain a DC component of the fluorescence signal of the sample;
    (g) wherein the fluorescence emission of the substrate is filtered and the DC component is proportional to the concentration of the fluorescence signal of the sample.

18. An apparatus for measuring a fluorescent sample on a substrate, the apparatus comprising:
    (a) a light source for exciting the fluocrescent sample for the generation of a sample fluorescent optical signal and a substrate fluorescent optical signal;
    (b) filtering apparatus for substantially eliminating the substrate fluorescent optical signal and leaving the sample fluorescent optical signal; and
    (c) processing apparatus for processing the sample fluorescence optical signal, wherein the filtering apparatus is an electrical filtering apparatus and comprises:
        (i) a modulator for modulating the frequency of the light source to excite fluorophore of the sample according to a predetermined modulation frequency such that a phase difference between the sample fluorescence optical signal and the substrate fluorescence optical signal is substantially 90 degrees;
        (ii) a signal generator for generating a sine wave signal based on a unity gain sine wave signal corresponding to the predetermined modulation frequency delayed by the phase of the substrate fluorescence optical signal;
        (iii) a mixer for mixing the sine wave signal with an acquired signal corresponding to the fluorescence emission of the sample and the substrate, into at least one mixed signal; and
        (iv) a filter for filtering the at least one mixed signal to obtain a DC component of the fluorescence signal of the sample.

19. An apparatus as claimed in claim 18,
    wherein the signal generator is further configured to generate the sine wave signal by generating a unity-gain square wave serving as a switching signal for mixing; and
    wherein the mixer is further configured to mix the unity-gain square wave with an acquired signal corresponding to the fluorescence emissions of the sample and the substrate, into the at least one mixed signal; and using the switching signal to modulate the sample fluorescence optical signal and the substrate fluorescence optical signal to create the phase difference between them.

20. The apparatus of claim 19, wherein the unity-gain square wave signal is in phase with the fluorescence signal of the sample.

21. An apparatus as claimed in claim 18,
wherein the modulator is further configured to modulate the frequency of light by modulating the frequency of a light source before introduction of the sample onto the substrate so as to generate the substrate fluorescence optical signal;
wherein the filtering apparatus further comprises a calibrator for generating a generated signal from the substrate fluorescence optical signal which is in phase with the substrate fluorescence optical signal;
and wherein the modulator is further configured to modulate the frequency of the light source to excite the fluorophore of the sample after introduction of the sample onto the substrate, according to a predetermined modulation frequency such that there exists the phase difference between the sample fluorescence optical signal and the substrate fluorescence optical signal.

22. The apparatus of claim 18, wherein the filter is a low-pass filter.

23. The apparatus of claim 18, wherein the acquired signal is acquired by an optical receiver.

24. The apparatus of claim 23, wherein the optical receiver is any one selected from the group consisting of: photodiode, avalanche photodiode, photomultiplier tube and CCD detector.

25. The apparatus of claim 18, wherein the unity-gain sine wave signal is generated by phase-locked loop (PLL) circuit.

26. The apparatus of claim 25, wherein the PLL circuit comprises a phase detector for generating an average DC voltage proportional to the phase difference, a low-pass filter (LPF1) for suppressing high frequency components generated by the phase detector and a voltage-controlled oscillator (VCO) for controlling the VCO frequency for oscillating at a frequency identical to the input frequency with a finite phase difference.

27. The apparatus of claim 18, wherein a quadrature phase shifter generates the two sine wave signals which are 90 degrees out of phase with each other.

28. The apparatus of claim 18, wherein the fluorophore label is fluorescein.

29. The apparatus of claim 18, wherein the light source is a 470 nm blue LED with 3460 mcd in intensity.

30. The apparatus of claim 18, wherein the substrate is a microfluidic substrate.

31. The apparatus of claim 18, further comprising an optical filter for filtering off signals with a wavelength outside a range of interest.

32. An apparatus for measuring a fluorescent sample on a substrate, the apparatus comprising:
(a) a modulator for modulating the frequency of the light source to excite the fluorophore of the sample according to a predetermined modulation frequency such that the phase difference between the sample fluorescence optical signal and the substrate fluorescence optical signal is substantially 90 degrees;
(b) a signal generator for generating a sine wave signal based on a unity-gain sine wave signal corresponding to the predetermined modulation frequency delayed by the phase of the substrate fluorescence optical signal;
(c) a mixer for mixing the sine wave signal with an acquired signal corresponding to the fluorescence emission of the sample and the substrate, into at least one mixed signal; and
(d) a filter for filtering the at least one mixed signal to obtain a DC component of the fluorescence signal of the sample.

33. An apparatus for measuring a fluorescent sample on a substrate, the apparatus comprising:
(a) a modulator for modulating the frequency of the light source to excite a fluorophore label of the sample according to a predetermined modulation frequency;
(b) a signal generator for generating a unity-gain square wave of the same frequency as a sample fluorescence optical signal; the unity-gain square wave serving as a switching signal for mixing;
(c) a mixer for mixing the unity-gain square wave with an acquired signal corresponding to the fluorescence emissions of the sample and the substrate, into at least one mixed signal; and for using the switching signal to modulate the sample fluorescence optical signal and a microfluidic substrate fluorescence optical signal to create a phase difference between them; and
(e) a filter for filtering the at least one mixed signal to obtain a DC component of the fluorescence signal of the sample.

34. An apparatus for measuring a fluorescent sample on a substrate, the apparatus comprising:
(a) a modulator for modulating the frequency of a light source before introduction of the sample onto the substrate so as to generate a substrate fluorescence optical signal;
(b) a calibrator for generating a generated signal from the substrate fluorescence optical signal and which is in phase with the substrate fluorescence optical signal;
(c) the modulator also for modulating the frequency of the light source to excite a fluorophore label of the sample, after introduction of the sample onto the substrate, according to a predetermined modulation frequency such that there exists a phase difference between the sample fluorescence optical signal and the substrate fluorescence optical signal;
(d) a signal generator for generating a sine wave signal based on a unity-gain sine wave signal corresponding to the predetermined modulation frequency and with a phase difference of 90 degrees with respect to the phase of the generated signal;
(e) a mixer for mixing the sine wave signal with an acquired signal corresponding to the fluorescence emission of the sample and the substrate, into at least one mixed signal; and
(f) a filter for filtering the at least one mixed signal to obtain a DC component of the fluorescence signal of the sample.

* * * * *